United States Patent
Dhawan et al.

(10) Patent No.: US 12,096,768 B2
(45) Date of Patent: Sep. 24, 2024

(54) POLYMERIC AND SOLID-SUPPORTED CHELATORS FOR STABILIZATION OF PERACID-CONTAINING COMPOSITIONS

(71) Applicant: ECOLAB USA INC., Saint Paul, MN (US)

(72) Inventors: Ashish Dhawan, Saint Paul, MN (US); Junzhong Li, Saint Paul, MN (US); David D. McSherry, Saint Paul, MN (US); Carter M. Silvernail, Saint Paul, MN (US); Chris Nagel, Saint Paul, MN (US)

(73) Assignee: ECOLAB USA INC., Saint Paul, MN (US)

( * ) Notice: Subject to any disclaimer, the term of this patent is extended or adjusted under 35 U.S.C. 154(b) by 40 days.

(21) Appl. No.: 16/947,585

(22) Filed: Aug. 7, 2020

(65) Prior Publication Data

US 2021/0037818 A1 Feb. 11, 2021

Related U.S. Application Data

(60) Provisional application No. 62/883,748, filed on Aug. 7, 2019.

(51) Int. Cl.
| | |
|---|---|
| *A01N 25/22* | (2006.01) |
| *A01N 37/16* | (2006.01) |
| *A01N 59/00* | (2006.01) |
| *C07C 407/00* | (2006.01) |
| *C08F 8/30* | (2006.01) |

(52) U.S. Cl.
CPC ............ *A01N 25/22* (2013.01); *A01N 37/16* (2013.01); *A01N 59/00* (2013.01); *C07C 407/006* (2013.01); *C08F 8/30* (2013.01)

(58) Field of Classification Search
CPC ........ A01N 25/22; A01N 37/16; A01N 59/00; C07C 407/006; C07C 8/30
See application file for complete search history.

(56) References Cited

U.S. PATENT DOCUMENTS

| | | | |
|---|---|---|---|
| 2,609,931 A | 9/1952 | Rodman et al. |
| 2,624,655 A | 1/1953 | Greenspan |
| 2,833,813 A | 5/1958 | Wallace |
| 2,877,266 A | 3/1959 | Malcolm |
| 2,955,905 A | 10/1960 | Daniel et al. |
| 3,048,624 A | 8/1962 | Dunn et al. |
| 3,053,633 A | 9/1962 | Dunlop et al. |
| 3,130,169 A | 4/1964 | Blumbergs et al. |
| 3,156,654 A | 11/1964 | Konecny et al. |
| 3,168,554 A | 2/1965 | Phillips et al. |
| 3,192,254 A | 6/1965 | Hayes |
| 3,256,198 A | 6/1966 | Matzner |
| 3,272,750 A | 9/1966 | Chase |
| 3,414,593 A | 12/1968 | Ronson |
| 3,432,546 A | 3/1969 | Oringer et al. |
| 3,847,830 A | 11/1974 | Williams et al. |
| 3,925,234 A | 12/1975 | Hachmann et al. |
| 3,956,159 A | 5/1976 | Jones |
| 3,969,258 A | 7/1976 | Carandang et al. |
| 4,003,841 A | 1/1977 | Hachmann et al. |
| 4,013,575 A | 3/1977 | Castrantas et al. |
| 4,051,058 A | 9/1977 | Bowing et al. |
| 4,051,059 A | 9/1977 | Bowing et al. |
| 4,100,095 A | 7/1978 | Hutchins et al. |
| 4,126,573 A | 11/1978 | Johnston |
| 4,129,517 A | 12/1978 | Eggensperger et al. |
| 4,144,179 A | 3/1979 | Chatterji |
| 4,170,453 A | 10/1979 | Kitko |
| 4,233,235 A | 11/1980 | Camden et al. |
| 4,259,201 A | 3/1981 | Cockrell, Jr. et al. |
| 4,297,298 A | 10/1981 | Crommelynck et al. |
| 4,311,598 A | 1/1982 | Verachtert |
| 4,367,156 A | 1/1983 | Diehl |
| 4,370,251 A | 1/1983 | Liao et al. |
| 4,374,035 A | 2/1983 | Bossu |
| 4,391,723 A | 7/1983 | Bacon et al. |
| 4,391,724 A | 7/1983 | Bacon |

(Continued)

FOREIGN PATENT DOCUMENTS

| | | |
|---|---|---|
| CA | 2016062 A1 | 11/1990 |
| CA | 2086003 A1 | 12/1991 |

(Continued)

OTHER PUBLICATIONS

Berro et al., "From Plastic to Silicone: The Novelties in Porous Polymer Fabrications", Journal of Nanomaterials, vol. 2015, Article ID 142195, 21 pages, Apr. 2, 2015.
Britannica Online Encyclopedia, "Surface coating: Polymers for surface coatings", https://www.britannica.com/print/article/575029, 4 pages, accessed Jul. 13, 2020.
Tan et al., "Hypercrosslinked porous polymer materials: design, synthesis, and applications", Chem. Soc. Rev., vol. 46, pp. 3322-3356 2017.
Wiley Online, "Polymers Coatings: Technology and Applications", https://www.wiley.com/en-us/PolymersCoatings%3A+Technology+and+Applications, accessed online on Jul. 16, 2020, published May 2020.
Wiley Online, "Porous Polymers", https://onlinelibrary.wiley.com/doi/book/10.1002/9780470929445, accessed online Jul. 16, 2020, published Jan. 25, 2011.

(Continued)

*Primary Examiner* — John Pak
*Assistant Examiner* — Nathan W Schlientz
(74) *Attorney, Agent, or Firm* — McKee, Voorhees & Sease, PLC

(57) ABSTRACT

Stabilized peroxycarboxylic acid compositions and the solid supported peracid stabilizers are provided. Methods of producing the solid supported peracid stabilizers are provided. The solid supported peracid stabilizers and the stable peroxycarboxylic acid compositions are particularly suitable for use in sanitizing equipment and surfaces to reduce yeasts, spores and bacteria, including those having contact with food, food products and/or components thereof, which require or benefit from infection control suitable for direct contact with such food sources.

12 Claims, 5 Drawing Sheets

(56) References Cited

U.S. PATENT DOCUMENTS

| | | |
|---|---|---|
| 4,412,934 A | 11/1983 | Chung et al. |
| 4,430,236 A | 2/1984 | Franks |
| 4,451,615 A | 5/1984 | Charnock |
| 4,470,919 A | 9/1984 | Goffinet et al. |
| 4,473,507 A | 9/1984 | Bossu |
| 4,483,778 A | 11/1984 | Thompson et al. |
| 4,486,327 A | 12/1984 | Murphy et al. |
| 4,529,534 A | 7/1985 | Richardson |
| 4,536,314 A | 8/1985 | Hardy et al. |
| 4,540,721 A | 9/1985 | Staller |
| 4,561,999 A | 12/1985 | Sekiguchi et al. |
| 4,563,112 A | 1/1986 | Mokuya et al. |
| 4,587,264 A | 5/1986 | Jourdan-Laforte et al. |
| 4,588,506 A | 5/1986 | Raymond et al. |
| 4,595,520 A | 6/1986 | Heile et al. |
| 4,617,090 A | 10/1986 | Chum et al. |
| 4,655,781 A | 4/1987 | Hsieh et al. |
| 4,661,280 A | 4/1987 | Ouhadi et al. |
| 4,681,592 A | 7/1987 | Hardy et al. |
| 4,743,447 A | 5/1988 | Le Rouzic et al. |
| 4,744,916 A | 5/1988 | Adams et al. |
| 4,769,168 A | 9/1988 | Ouhadi et al. |
| 4,778,618 A | 10/1988 | Fong et al. |
| 4,783,278 A | 11/1988 | Sanderson et al. |
| 4,786,431 A | 11/1988 | Broze et al. |
| 4,797,225 A | 1/1989 | Broze et al. |
| 4,820,440 A | 4/1989 | Hemm et al. |
| 4,846,992 A | 7/1989 | Fonsny et al. |
| 4,853,143 A | 8/1989 | Hardy et al. |
| 4,879,057 A | 11/1989 | Dankowski et al. |
| 4,909,953 A | 3/1990 | Sadlowski et al. |
| 4,917,815 A | 4/1990 | Beilfuss et al. |
| 4,957,647 A | 9/1990 | Zielske |
| 4,964,870 A | 10/1990 | Fong et al. |
| 5,004,558 A | 4/1991 | Dyroff et al. |
| 5,019,292 A | 5/1991 | Baeck et al. |
| 5,030,240 A | 7/1991 | Wiersema et al. |
| 5,073,285 A | 12/1991 | Liberati et al. |
| 5,098,598 A | 3/1992 | Sankey et al. |
| 5,117,049 A | 5/1992 | Venturello et al. |
| 5,139,788 A | 8/1992 | Schmidt |
| 5,143,641 A | 9/1992 | Nunn |
| 5,160,656 A | 11/1992 | Carron et al. |
| 5,196,133 A | 3/1993 | Leslie et al. |
| 5,200,189 A | 4/1993 | Oakes et al. |
| 5,246,620 A | 9/1993 | Gethoeffer et al. |
| 5,250,212 A | 10/1993 | De Buzzaccarini et al. |
| 5,250,707 A | 10/1993 | Inaba et al. |
| 5,264,229 A | 11/1993 | Mannig et al. |
| 5,266,587 A | 11/1993 | Sankey et al. |
| 5,268,003 A | 12/1993 | Coope et al. |
| 5,274,369 A | 12/1993 | Tsunoda et al. |
| 5,281,351 A | 1/1994 | Romeo et al. |
| 5,288,746 A | 2/1994 | Pramod |
| 5,296,239 A | 3/1994 | Colery et al. |
| 5,310,774 A | 5/1994 | Farrar |
| 5,314,687 A | 5/1994 | Oakes et al. |
| 5,340,501 A | 8/1994 | Steindorf |
| 5,344,652 A | 9/1994 | Hall, II et al. |
| 5,349,083 A | 9/1994 | Brougham et al. |
| 5,362,899 A | 11/1994 | Campbell |
| 5,374,369 A | 12/1994 | Angevaare et al. |
| 5,382,571 A | 1/1995 | Granger et al. |
| 5,383,977 A | 1/1995 | Pearce |
| 5,391,324 A | 2/1995 | Reinhardt et al. |
| 5,398,506 A | 3/1995 | Martin |
| 5,409,629 A | 4/1995 | Shulman et al. |
| 5,409,713 A | 4/1995 | Lokkesmoe et al. |
| 5,415,807 A | 5/1995 | Gosselink et al. |
| 5,422,028 A | 6/1995 | Oakes et al. |
| 5,431,848 A | 7/1995 | Getty |
| 5,431,849 A | 7/1995 | Damhus et al. |
| 5,433,881 A | 7/1995 | Townend et al. |
| 5,435,808 A | 7/1995 | Holzhauer et al. |
| 5,437,686 A | 8/1995 | Heffner et al. |
| 5,447,648 A | 9/1995 | Steindorf |
| 5,453,214 A | 9/1995 | van den Berg et al. |
| 5,454,563 A | 10/1995 | Nagamoto et al. |
| 5,463,112 A | 10/1995 | Sankey et al. |
| 5,464,563 A | 11/1995 | Moore et al. |
| 5,466,825 A | 11/1995 | Carr et al. |
| 5,472,619 A | 12/1995 | Holzhauer et al. |
| 5,475,123 A | 12/1995 | Bos |
| 5,486,212 A | 1/1996 | Mitchell et al. |
| 5,496,728 A | 3/1996 | Hardy et al. |
| 5,503,765 A | 4/1996 | Schepers et al. |
| 5,505,740 A | 4/1996 | Kong et al. |
| 5,525,121 A | 6/1996 | Heffner et al. |
| 5,545,374 A | 8/1996 | French et al. |
| 5,565,231 A | 10/1996 | Malone et al. |
| 5,576,282 A | 11/1996 | Miracle et al. |
| 5,578,134 A | 11/1996 | Lentsch et al. |
| 5,589,507 A | 12/1996 | Hall, II et al. |
| 5,595,967 A | 1/1997 | Miracle et al. |
| 5,599,781 A | 2/1997 | Haeggberg et al. |
| 5,616,281 A | 4/1997 | Hardy et al. |
| 5,617,710 A | 4/1997 | Goossens et al. |
| 5,624,634 A | 4/1997 | Brougham et al. |
| 5,632,676 A | 5/1997 | Kurschner et al. |
| 5,635,195 A | 6/1997 | Hall, II et al. |
| 5,637,755 A | 6/1997 | Nagumo et al. |
| 5,647,997 A | 7/1997 | Holzhauer et al. |
| 5,672,739 A | 9/1997 | Varadaraj et al. |
| 5,681,805 A | 10/1997 | Scheuing et al. |
| 5,683,724 A | 11/1997 | Hei et al. |
| 5,683,977 A | 11/1997 | Jureller et al. |
| 5,691,298 A | 11/1997 | Gosselink et al. |
| 5,698,326 A | 12/1997 | Wilson et al. |
| 5,698,506 A | 12/1997 | Angevaare et al. |
| 5,716,923 A | 2/1998 | MacBeath |
| 5,718,910 A | 2/1998 | Oakes et al. |
| 5,755,977 A | 5/1998 | Gurol et al. |
| 5,767,308 A | 6/1998 | Thiele et al. |
| 5,780,064 A | 7/1998 | Meisters et al. |
| 5,785,867 A | 7/1998 | Lazonby et al. |
| 5,814,592 A | 9/1998 | Kahn et al. |
| 5,817,614 A | 10/1998 | Miracle et al. |
| 5,827,447 A | 10/1998 | Tamura et al. |
| 5,827,808 A | 10/1998 | Appleby et al. |
| 5,840,343 A | 11/1998 | Hall, II et al. |
| 5,872,092 A | 2/1999 | Kong-Chan et al. |
| 5,880,083 A | 3/1999 | Beaujean et al. |
| 5,900,187 A | 5/1999 | Scialla et al. |
| 5,900,256 A | 5/1999 | Scoville, Jr. et al. |
| 5,914,303 A | 6/1999 | Sankey et al. |
| 5,928,382 A | 7/1999 | Reinhardt et al. |
| 5,929,012 A | 7/1999 | Del Duca et al. |
| 5,965,033 A | 10/1999 | Huss et al. |
| 5,965,785 A | 10/1999 | Braden et al. |
| 5,968,885 A | 10/1999 | Del Duca et al. |
| 5,968,893 A | 10/1999 | Manohar et al. |
| 5,977,403 A | 11/1999 | Byers |
| 5,998,350 A | 12/1999 | Burns et al. |
| 6,004,922 A | 12/1999 | Watson et al. |
| 6,007,627 A | 12/1999 | Barnholtz |
| 6,010,729 A | 1/2000 | Gutzmann et al. |
| 6,014,536 A | 1/2000 | Ban et al. |
| 6,022,381 A | 2/2000 | Dias et al. |
| 6,024,986 A | 2/2000 | Hei |
| 6,049,002 A | 4/2000 | Mattila et al. |
| 6,103,286 A | 8/2000 | Gutzmann et al. |
| 6,110,883 A | 8/2000 | Petri et al. |
| 6,136,769 A | 10/2000 | Asano et al. |
| 6,156,129 A | 12/2000 | Hlivka et al. |
| 6,156,156 A | 12/2000 | Rousu et al. |
| 6,165,483 A | 12/2000 | Hei et al. |
| 6,177,393 B1 | 1/2001 | McGregor et al. |
| 6,183,763 B1 | 2/2001 | Beerse et al. |
| 6,183,807 B1 | 2/2001 | Gutzmann et al. |
| 6,196,719 B1 | 3/2001 | Brown |
| 6,201,110 B1 | 3/2001 | Olsen et al. |
| 6,207,632 B1 | 3/2001 | Brooker et al. |
| 6,211,237 B1 | 4/2001 | Huss et al. |
| 6,218,429 B1 | 4/2001 | Ohkawa et al. |

(56) References Cited

U.S. PATENT DOCUMENTS

| | | | |
|---|---|---|---|
| 6,221,341 B1 | 4/2001 | Montgomery |
| 6,238,685 B1 | 5/2001 | Hei et al. |
| 6,257,253 B1 | 7/2001 | Lentsch et al. |
| 6,262,013 B1 | 7/2001 | Smith et al. |
| 6,274,542 B1 | 8/2001 | Carr et al. |
| 6,277,804 B1 | 8/2001 | Kahn et al. |
| 6,284,793 B1 | 9/2001 | Fuchs et al. |
| 6,294,186 B1 | 9/2001 | Beerse et al. |
| 6,310,025 B1 | 10/2001 | Del Duca et al. |
| 6,326,032 B1 | 12/2001 | Richter et al. |
| 6,346,279 B1 | 2/2002 | Rochon |
| 6,384,008 B1 | 5/2002 | Parry |
| 6,399,564 B1 | 6/2002 | Speed et al. |
| 6,407,052 B2 | 6/2002 | Gassenmeier et al. |
| 6,417,151 B1 | 7/2002 | Grothus et al. |
| 6,432,661 B1 | 8/2002 | Heitfeld et al. |
| 6,436,885 B2 | 8/2002 | Biedermann et al. |
| 6,444,634 B1 | 9/2002 | Mason et al. |
| 6,468,472 B1 | 10/2002 | Yu et al. |
| 6,503,876 B1 | 1/2003 | Broeckx |
| 6,528,471 B1 | 3/2003 | Del Duca et al. |
| 6,537,958 B1 | 3/2003 | Di Capua et al. |
| 6,545,047 B2 | 4/2003 | Gutzmann et al. |
| 6,548,467 B2 | 4/2003 | Baker et al. |
| 6,548,470 B1 | 4/2003 | De Buzzaccarini et al. |
| 6,566,318 B2 | 5/2003 | Perkins et al. |
| 6,569,286 B1 | 5/2003 | Withenshaw et al. |
| 6,576,335 B2 * | 6/2003 | Harrup .................... B01J 45/00 428/325 |
| 6,576,602 B1 | 6/2003 | Smerznak et al. |
| 6,589,565 B1 | 7/2003 | Richter et al. |
| 6,599,871 B2 | 7/2003 | Smith |
| 6,602,845 B2 | 8/2003 | Connor et al. |
| 6,607,710 B1 | 8/2003 | Ito et al. |
| 6,627,593 B2 | 9/2003 | Hei et al. |
| 6,627,594 B1 | 9/2003 | James et al. |
| 6,627,657 B1 | 9/2003 | Hilgren et al. |
| 6,635,286 B2 | 10/2003 | Hei et al. |
| 6,649,140 B2 | 11/2003 | Paparatto et al. |
| 6,660,707 B2 | 12/2003 | Lentsch et al. |
| 6,686,324 B2 | 2/2004 | Ramirez |
| 6,689,732 B1 | 2/2004 | Guedira et al. |
| 6,693,069 B2 | 2/2004 | Koerber et al. |
| 6,696,093 B2 | 2/2004 | Ney et al. |
| 6,699,828 B1 | 3/2004 | De Buzzaccarini et al. |
| 6,758,967 B1 | 7/2004 | Anderson, Jr. et al. |
| 6,770,774 B2 | 8/2004 | Van De Bovenkamp-Bouwman et al. |
| 6,774,082 B2 | 8/2004 | Bruening et al. |
| 6,803,057 B2 | 10/2004 | Ramirez et al. |
| 6,806,246 B2 | 10/2004 | Preissner et al. |
| 6,830,591 B1 | 12/2004 | Wang et al. |
| 6,841,090 B1 | 1/2005 | Serego et al. |
| 6,866,749 B2 | 3/2005 | Delmas et al. |
| 6,878,680 B2 | 4/2005 | Kitko et al. |
| 6,919,304 B2 | 7/2005 | Dykstra et al. |
| 7,012,053 B1 | 3/2006 | Barnabas et al. |
| 7,012,154 B2 | 3/2006 | Vineyard et al. |
| 7,060,136 B1 | 6/2006 | Zeiher et al. |
| 7,078,373 B2 | 7/2006 | Burrows et al. |
| 7,148,351 B2 | 12/2006 | Morris et al. |
| 7,169,236 B2 | 1/2007 | Zeiher et al. |
| 7,189,385 B2 | 3/2007 | Montgomery |
| 7,217,295 B2 | 5/2007 | Samain et al. |
| 7,243,664 B2 | 7/2007 | Berger et al. |
| 7,335,629 B2 | 2/2008 | Gentschev et al. |
| 7,431,775 B2 | 10/2008 | Wang et al. |
| 7,448,255 B2 | 11/2008 | Hoots et al. |
| 7,494,963 B2 | 2/2009 | Ahmed et al. |
| 7,498,051 B2 | 3/2009 | Man et al. |
| 7,524,803 B2 | 4/2009 | Lentsch et al. |
| 7,541,324 B2 | 6/2009 | Reinhardt et al. |
| 7,569,232 B2 | 8/2009 | Man et al. |
| 7,569,528 B2 | 8/2009 | Lant et al. |
| 7,598,218 B2 | 10/2009 | Stolte et al. |
| 7,601,789 B2 | 10/2009 | Morris et al. |
| 7,618,545 B2 | 11/2009 | Wakao et al. |
| 7,682,403 B2 | 3/2010 | Gohl et al. |
| 7,686,892 B2 | 3/2010 | Smets et al. |
| 7,723,083 B2 | 5/2010 | DiCosimo et al. |
| 7,771,737 B2 | 8/2010 | Man et al. |
| 7,863,234 B2 | 1/2011 | Maki et al. |
| 7,875,720 B2 | 1/2011 | Morris et al. |
| 7,887,641 B2 | 2/2011 | Man et al. |
| 7,910,371 B2 | 3/2011 | Johnson |
| 7,915,445 B2 | 3/2011 | Maatta et al. |
| 7,919,122 B2 | 4/2011 | Okano et al. |
| 7,922,828 B2 | 4/2011 | Smith et al. |
| 7,949,432 B2 | 5/2011 | Rice |
| 7,981,679 B2 | 7/2011 | Rice |
| 7,985,318 B2 | 7/2011 | Shevchenko et al. |
| 8,017,409 B2 | 9/2011 | Tokhtuev et al. |
| 8,030,351 B2 | 10/2011 | Gutzmann et al. |
| 8,071,528 B2 | 12/2011 | Smith et al. |
| 8,080,404 B1 | 12/2011 | Turetsky et al. |
| 8,084,756 B2 | 12/2011 | Tokhtuev et al. |
| 8,110,603 B2 | 2/2012 | Kawabata et al. |
| 8,119,412 B2 | 2/2012 | Kraus |
| 8,153,573 B2 | 4/2012 | Miralles et al. |
| 8,178,336 B2 | 5/2012 | Derkx et al. |
| 8,226,939 B2 | 7/2012 | Herdt et al. |
| 8,231,917 B2 | 7/2012 | Herdt et al. |
| 8,236,573 B2 | 8/2012 | Tokhtuev et al. |
| 8,241,624 B2 | 8/2012 | Herdt et al. |
| 8,309,507 B2 | 11/2012 | Fernandez Prieto et al. |
| 8,344,026 B2 | 1/2013 | Li et al. |
| 8,426,634 B2 | 4/2013 | Neas et al. |
| 8,568,613 B2 | 10/2013 | Man et al. |
| 8,729,296 B2 | 5/2014 | Fast et al. |
| 8,822,719 B1 | 9/2014 | Li et al. |
| 9,005,669 B2 | 4/2015 | Allen et al. |
| 9,012,504 B2 | 4/2015 | Olson et al. |
| 9,034,390 B2 | 5/2015 | Kielbania |
| 9,288,992 B2 | 3/2016 | Li et al. |
| 9,321,664 B2 | 4/2016 | Li et al. |
| 9,585,397 B2 | 3/2017 | Li et al. |
| 9,624,119 B2 | 4/2017 | Dotzauer et al. |
| 9,676,711 B2 | 6/2017 | Junzhong et al. |
| 9,701,931 B2 | 7/2017 | Moore |
| 9,752,105 B2 | 9/2017 | Stokes et al. |
| 9,902,627 B2 | 2/2018 | Li et al. |
| 10,017,720 B2 | 7/2018 | Li et al. |
| 10,165,774 B2 | 1/2019 | Li et al. |
| 10,370,621 B2 | 8/2019 | Gaulard et al. |
| 10,654,025 B2 | 5/2020 | Choi et al. |
| 11,026,421 B2 | 6/2021 | Li et al. |
| 2001/0054201 A1 | 12/2001 | Wang et al. |
| 2002/0007516 A1 | 1/2002 | Wang |
| 2002/0040151 A1 | 4/2002 | Fontenot et al. |
| 2002/0055043 A1 | 5/2002 | Morikawa et al. |
| 2002/0064565 A1 | 5/2002 | Karagoezian |
| 2002/0086903 A1 | 7/2002 | Giambrone et al. |
| 2002/0102702 A1 | 8/2002 | Osten et al. |
| 2002/0128312 A1 | 9/2002 | Hei et al. |
| 2002/0157189 A1 | 10/2002 | Wang et al. |
| 2002/0160928 A1 | 10/2002 | Smerznak et al. |
| 2002/0161258 A1 | 10/2002 | Miracle et al. |
| 2002/0169088 A1 | 11/2002 | Wang |
| 2002/0188026 A1 | 12/2002 | Singh et al. |
| 2002/0193626 A1 | 12/2002 | Pohjanvesi et al. |
| 2003/0012681 A1 | 1/2003 | Yeganeh et al. |
| 2003/0045443 A1 | 3/2003 | Korber et al. |
| 2003/0100468 A1 | 5/2003 | Smerznak et al. |
| 2003/0100469 A1 | 5/2003 | Connor et al. |
| 2003/0119699 A1 | 6/2003 | Miracle et al. |
| 2003/0148909 A1 | 8/2003 | Del Duca et al. |
| 2003/0154556 A1 | 8/2003 | Del Duca et al. |
| 2003/0180377 A1 | 9/2003 | Ramirez et al. |
| 2003/0234382 A1 | 12/2003 | Sato et al. |
| 2003/0235623 A1 | 12/2003 | Van Oosterom |
| 2004/0002616 A1 | 1/2004 | Preto et al. |
| 2004/0010858 A1 | 1/2004 | Detering et al. |
| 2004/0016060 A1 | 1/2004 | Detering et al. |
| 2004/0025262 A1 | 2/2004 | Hamers et al. |

(56) References Cited

U.S. PATENT DOCUMENTS

| | | |
|---|---|---|
| 2004/0033269 A1 | 2/2004 | Hei et al. |
| 2004/0035537 A1 | 2/2004 | Delmas et al. |
| 2004/0072718 A1 | 4/2004 | Price et al. |
| 2004/0077514 A1 | 4/2004 | Price et al. |
| 2004/0107506 A1 | 6/2004 | Detering et al. |
| 2004/0139559 A1 | 7/2004 | Detering et al. |
| 2004/0266653 A1 | 12/2004 | Delplancke et al. |
| 2005/0000908 A1 | 1/2005 | Karlsson et al. |
| 2005/0008526 A1 | 1/2005 | Bianchetti et al. |
| 2005/0146305 A1 | 7/2005 | Kneller |
| 2005/0222003 A1 | 10/2005 | Gagliardi et al. |
| 2005/0226800 A1 | 10/2005 | Wang et al. |
| 2005/0241817 A1 | 11/2005 | Moore et al. |
| 2005/0281773 A1 | 12/2005 | Wieland et al. |
| 2005/0288204 A1 | 12/2005 | Matts et al. |
| 2006/0040847 A1 | 2/2006 | Weibel |
| 2006/0043340 A1 | 3/2006 | Koizumi et al. |
| 2006/0065469 A1 | 3/2006 | Stefano et al. |
| 2006/0088498 A1 | 4/2006 | Martin et al. |
| 2006/0172909 A1 | 8/2006 | Schmiedel et al. |
| 2006/0173209 A1 | 8/2006 | Vineyard et al. |
| 2006/0199742 A1 | 9/2006 | Arisz et al. |
| 2006/0247151 A1 | 11/2006 | Kaaret et al. |
| 2006/0254001 A1 | 11/2006 | Hoeffkes et al. |
| 2006/0257964 A1 | 11/2006 | Larose |
| 2006/0276366 A1 | 12/2006 | Deljosevic et al. |
| 2006/0289364 A1 | 12/2006 | Wakao et al. |
| 2007/0010420 A1 | 1/2007 | Lange et al. |
| 2007/0042924 A1 | 2/2007 | DiCosimo et al. |
| 2007/0087954 A1 | 4/2007 | Wang et al. |
| 2007/0093407 A1 | 4/2007 | Bianchetti et al. |
| 2007/0102359 A1 | 5/2007 | Lombardi et al. |
| 2007/0105744 A1 | 5/2007 | Amiconi et al. |
| 2007/0113875 A1 | 5/2007 | Wang et al. |
| 2007/0163779 A1 | 7/2007 | Rae et al. |
| 2007/0173430 A1 | 7/2007 | Souter et al. |
| 2007/0225197 A1 | 9/2007 | Kruse et al. |
| 2007/0281002 A1 | 12/2007 | Morales et al. |
| 2008/0001125 A1 | 1/2008 | Zetlmeisl et al. |
| 2008/0064619 A1 | 3/2008 | Bastigkeit et al. |
| 2008/0089364 A1 | 4/2008 | Barry et al. |
| 2008/0095677 A1 | 4/2008 | McSherry et al. |
| 2008/0095861 A1 | 4/2008 | Walker |
| 2008/0146482 A1 | 6/2008 | Schneiderman et al. |
| 2008/0176784 A1 | 7/2008 | Clowes et al. |
| 2008/0194449 A1 | 8/2008 | Becker et al. |
| 2008/0200364 A1 | 8/2008 | Garaffa et al. |
| 2008/0312107 A1 | 12/2008 | Harris et al. |
| 2009/0005286 A1 | 1/2009 | Detering et al. |
| 2009/0011971 A1 | 1/2009 | Evers |
| 2009/0018049 A1 | 1/2009 | Stolte et al. |
| 2009/0043123 A1 | 2/2009 | Copenhafer et al. |
| 2009/0047176 A1 | 2/2009 | Cregger et al. |
| 2009/0061017 A1 | 3/2009 | Pedersen et al. |
| 2009/0075856 A1 | 3/2009 | Schmiedel et al. |
| 2009/0088347 A1 | 4/2009 | Mukhopadhyay et al. |
| 2009/0145202 A1 | 6/2009 | Tokhtuev et al. |
| 2009/0148686 A1 | 6/2009 | Urankar et al. |
| 2009/0175956 A1 | 7/2009 | Buschmann et al. |
| 2009/0188055 A1 | 7/2009 | Bernhardt et al. |
| 2009/0221704 A1 | 9/2009 | Aksela et al. |
| 2009/0249557 A1 | 10/2009 | Maki et al. |
| 2009/0263904 A1 | 10/2009 | Clinton et al. |
| 2009/0269324 A1 | 10/2009 | Herdt et al. |
| 2009/0294382 A1 | 12/2009 | Fukuyo et al. |
| 2010/0002115 A1 | 1/2010 | Liu |
| 2010/0021557 A1 | 1/2010 | Li et al. |
| 2010/0021558 A1 | 1/2010 | Dada et al. |
| 2010/0041579 A1 | 2/2010 | Bianchetti et al. |
| 2010/0041752 A1 | 2/2010 | Dicosimo et al. |
| 2010/0048730 A1 | 2/2010 | Li et al. |
| 2010/0084603 A1 | 4/2010 | Narayan et al. |
| 2010/0108566 A1 | 5/2010 | Scattergood et al. |
| 2010/0120913 A1 | 5/2010 | Larson et al. |
| 2010/0140186 A1 | 6/2010 | Huang et al. |
| 2010/0143491 A1 | 6/2010 | Kawabata et al. |
| 2010/0160449 A1 | 6/2010 | Rovison, Jr. et al. |
| 2010/0222242 A1 | 9/2010 | Huang et al. |
| 2010/0227000 A1 | 9/2010 | Board et al. |
| 2010/0227829 A1 | 9/2010 | Licari et al. |
| 2010/0275382 A1 | 11/2010 | Calvert |
| 2010/0286017 A1 | 11/2010 | Righetto |
| 2010/0308260 A1 | 12/2010 | Maki et al. |
| 2011/0052445 A1 | 3/2011 | Herdt et al. |
| 2011/0146707 A1 | 6/2011 | Cermenati et al. |
| 2011/0168567 A1 | 7/2011 | Smith et al. |
| 2011/0169270 A1 | 7/2011 | Todorof |
| 2011/0171062 A1 | 7/2011 | Wolfe |
| 2011/0173897 A1 | 7/2011 | Schneider |
| 2011/0177145 A1 | 7/2011 | Erkenbrecher et al. |
| 2011/0217761 A1 | 9/2011 | Hilgren et al. |
| 2011/0226293 A1 | 9/2011 | Bonnechere et al. |
| 2011/0230380 A1 | 9/2011 | Holzhauer et al. |
| 2011/0240510 A1 | 10/2011 | De Poortere et al. |
| 2011/0257060 A1 | 10/2011 | Dykstra |
| 2011/0274974 A1 | 11/2011 | Sabi et al. |
| 2011/0311645 A1 | 12/2011 | Diaz |
| 2012/0012307 A1 | 1/2012 | Nevin |
| 2012/0024525 A1 | 2/2012 | Svarczkopf et al. |
| 2012/0052134 A1 | 3/2012 | Li et al. |
| 2012/0070339 A1 | 3/2012 | Lawal |
| 2012/0085236 A1 | 4/2012 | McCorriston et al. |
| 2012/0085931 A1 | 4/2012 | Burns et al. |
| 2012/0097614 A1 | 4/2012 | Silva et al. |
| 2012/0149121 A1 | 6/2012 | Tokhtuev et al. |
| 2012/0164236 A1 | 6/2012 | Iwasa et al. |
| 2012/0172440 A1 | 7/2012 | Li et al. |
| 2012/0172441 A1 | 7/2012 | Li et al. |
| 2012/0225943 A1 | 9/2012 | Gohl et al. |
| 2012/0321510 A1 | 12/2012 | Herdt et al. |
| 2013/0018097 A1 | 1/2013 | Bolduc et al. |
| 2013/0022496 A1 | 1/2013 | Herdt et al. |
| 2013/0053512 A1 | 2/2013 | Kojima et al. |
| 2013/0063512 A1 | 3/2013 | Takagi et al. |
| 2013/0143786 A1 | 6/2013 | Zhu et al. |
| 2013/0210923 A1 | 8/2013 | Zhu |
| 2013/0247308 A1 | 9/2013 | Duerrschmidt et al. |
| 2013/0251590 A1* | 9/2013 | Golden ............... A01N 59/00 422/24 |
| 2014/0096971 A1 | 4/2014 | Keizer et al. |
| 2014/0097144 A1 | 4/2014 | Li et al. |
| 2014/0120179 A1 | 5/2014 | Smith et al. |
| 2014/0121272 A1 | 5/2014 | Smith et al. |
| 2014/0255514 A1 | 9/2014 | Li et al. |
| 2014/0256811 A1 | 9/2014 | Li et al. |
| 2014/0335199 A1 | 11/2014 | Li et al. |
| 2016/0150779 A1 | 6/2016 | Li et al. |
| 2016/0176814 A1 | 6/2016 | Balasubramanian et al. |
| 2016/0176815 A1 | 6/2016 | Li et al. |
| 2016/0200595 A1 | 7/2016 | Li et al. |
| 2016/0348037 A1 | 12/2016 | Findlay et al. |
| 2017/0020130 A1 | 1/2017 | Buschmann et al. |
| 2017/0064949 A1 | 3/2017 | Kraus et al. |
| 2017/0118989 A1 | 5/2017 | Oppong et al. |
| 2017/0245499 A1 | 8/2017 | Fast et al. |
| 2018/0178191 A1 | 6/2018 | Schwab et al. |
| 2018/0187129 A1 | 7/2018 | Traistaru et al. |
| 2019/0016678 A1 | 1/2019 | Ganguly-Mink et al. |
| 2019/0069547 A1 | 3/2019 | Kraus et al. |
| 2019/0208780 A1 | 7/2019 | McSherry et al. |

FOREIGN PATENT DOCUMENTS

| | | |
|---|---|---|
| CA | 1300465 C | 5/1992 |
| CA | 1305721 C | 7/1992 |
| CA | 2325709 A1 | 5/2001 |
| CN | 1751768 A | 3/2006 |
| CN | 101314632 A | 12/2008 |
| CN | 100486668 C | 5/2009 |
| DE | 1024514 B | 2/1958 |
| DE | 2451904 A1 | 5/1975 |
| DE | 2616049 A1 | 10/1977 |
| DE | 19754290 A1 | 6/1999 |
| DE | 19853845 A1 | 5/2000 |

(56) References Cited

FOREIGN PATENT DOCUMENTS

| | | |
|---|---|---|
| DE | 10011273 A1 | 9/2001 |
| EP | 0061393 A1 | 9/1982 |
| EP | 0068547 A1 | 1/1983 |
| EP | 0075419 A2 | 3/1983 |
| EP | 0231632 A2 | 8/1987 |
| EP | 267175 A2 | 5/1988 |
| EP | 0273775 A2 | 7/1988 |
| EP | 0280697 A1 | 9/1988 |
| EP | 0334427 A1 | 9/1989 |
| EP | 0384911 A2 | 8/1990 |
| EP | 0387049 A2 | 9/1990 |
| EP | 0396341 A2 | 11/1990 |
| EP | 0415028 A1 | 3/1991 |
| EP | 0442549 A2 | 8/1991 |
| EP | 0626371 A1 | 11/1994 |
| EP | 0741776 A1 | 11/1996 |
| EP | 0751210 A1 | 1/1997 |
| EP | 0822183 A2 | 2/1998 |
| EP | 0845526 A2 | 6/1998 |
| EP | 0906950 A1 | 4/1999 |
| EP | 1001012 A1 | 5/2000 |
| EP | 1041417 A2 | 10/2000 |
| EP | 1114137 B1 | 7/2004 |
| EP | 1129171 B1 | 8/2005 |
| EP | 1717302 B1 | 4/2008 |
| EP | 2271410 A2 | 1/2011 |
| EP | 2329893 A1 | 6/2011 |
| EP | 2522714 A1 | 11/2012 |
| EP | 2522715 A1 | 11/2012 |
| EP | 2222685 B1 | 7/2014 |
| EP | 2714877 B1 | 7/2017 |
| EP | 2566943 B1 | 9/2017 |
| GB | 1198734 A | 7/1970 |
| GB | 1584170 A | 2/1981 |
| GB | 2179364 A | 3/1987 |
| GB | 2179365 A | 3/1987 |
| GB | 2187199 A | 9/1987 |
| GB | 2195124 A | 3/1988 |
| GB | 2195125 A | 3/1988 |
| GB | 2195649 A | 4/1988 |
| GB | 2208233 A | 3/1989 |
| GB | 2279660 A | 1/1995 |
| GB | 2281744 A | 3/1995 |
| GB | 2361687 A | 10/2000 |
| JP | S62155203 A | 7/1987 |
| JP | H05140079 A | 6/1993 |
| JP | H05186989 A | 7/1993 |
| JP | H0892594 A | 4/1996 |
| JP | H0892595 A | 4/1996 |
| JP | H08143898 A | 6/1996 |
| JP | H08245549 A | 9/1996 |
| JP | 3119174 B2 | 12/2000 |
| JP | 2000357633 A | 12/2000 |
| JP | 2002105352 A | 4/2002 |
| JP | 2006045146 A | 2/2006 |
| JP | 2006045147 A | 2/2006 |
| JP | 2007084589 A | 4/2007 |
| JP | 2008092594 A | 4/2008 |
| JP | 2008245549 A | 10/2008 |
| KR | 20060007497 A | 1/2006 |
| WO | 9007501 A1 | 7/1990 |
| WO | 9106574 A1 | 5/1991 |
| WO | 9107375 A1 | 5/1991 |
| WO | 9114674 A2 | 10/1991 |
| WO | 9115474 A1 | 10/1991 |
| WO | 9208471 A1 | 5/1992 |
| WO | 9403395 A1 | 2/1994 |
| WO | 9403580 A1 | 2/1994 |
| WO | 9410284 A1 | 5/1994 |
| WO | 9413776 A1 | 6/1994 |
| WO | 9418299 A1 | 8/1994 |
| WO | 9419446 A1 | 9/1994 |
| WO | 9424869 A1 | 11/1994 |
| WO | 9429509 A1 | 12/1994 |
| WO | 9502030 A1 | 1/1995 |
| WO | 9504128 A1 | 2/1995 |
| WO | 9521122 A1 | 8/1995 |
| WO | 9521290 A1 | 8/1995 |
| WO | 9533816 A1 | 12/1995 |
| WO | 9610072 A1 | 4/1996 |
| WO | 9614384 A1 | 5/1996 |
| WO | 9616148 A1 | 5/1996 |
| WO | 9633254 A1 | 10/1996 |
| WO | 9700938 A1 | 1/1997 |
| WO | 9742286 A1 | 11/1997 |
| WO | 9743393 A2 | 11/1997 |
| WO | 9800528 A1 | 1/1998 |
| WO | 9803513 A1 | 1/1998 |
| WO | 9804659 A2 | 2/1998 |
| WO | 9805749 A1 | 2/1998 |
| WO | 9811189 A1 | 3/1998 |
| WO | 9818893 A1 | 5/1998 |
| WO | 9919451 A1 | 4/1999 |
| WO | 9931215 A1 | 6/1999 |
| WO | 9932598 A1 | 7/1999 |
| WO | 9964556 A1 | 12/1999 |
| WO | 0042145 A1 | 7/2000 |
| WO | 0042158 A1 | 7/2000 |
| WO | 0078911 A1 | 12/2000 |
| WO | 200144176 A1 | 6/2001 |
| WO | 0187358 A1 | 11/2001 |
| WO | 2005067741 A1 | 7/2005 |
| WO | 2006016145 A1 | 2/2006 |
| WO | 2006094232 A1 | 9/2006 |
| WO | 2006131503 A2 | 12/2006 |
| WO | 2007066302 A2 | 6/2007 |
| WO | 2009071664 A1 | 6/2009 |
| WO | 2009141548 A2 | 11/2009 |
| WO | 2010050634 A1 | 5/2010 |
| WO | 2011089313 A2 | 7/2011 |
| WO | 2012080124 A1 | 6/2012 |
| WO | 2014137605 A1 | 9/2014 |
| WO | 2020028657 A1 | 2/2020 |
| WO | 2020069078 A1 | 4/2020 |

OTHER PUBLICATIONS

Wu et al., "Porous Polymers as Multifunctional Material Platforms toward Task-Specific Applications", Advanced Materials, vol. 31, 45 pages, 2019.

Chessa et al., "Sorption and Separation of Palladium, Platinum and Gold Chlorocomplexes by Means of a Dipicolinic Acid Polystyrene-Based Chelating Resin", Reactive Polymers, vol. 14, pp. 143-150, 1991.

Sadia et al., "Comparison of Simple and Chelated Amberlite IR-120 for Preconcentration and Determination of Cu(II) from Aqueous Samples", Bull. Chem. Soc. Ethiop., vol. 30(1), pp. 39-54, 2016.

Salih et al., "Sorption of Lead, Zinc and Copper from Simulated Wastewater by Amberlite Ir-120 Resin", Journal of Engineering, vol. 18, No. 9, pp. 1042-1054, Sep. 2012.

International Searching Authority in connection with PCT/US20/45313 filed Aug. 7, 2020, "The International Search Report and the Written Opinion of the International Searching Authority, or the Declaration", 17 pages, mailed Dec. 10, 2020.

Brooks et al., "Alkaline hydrogen peroxide bleaching of cellulose," Cellulose, Sep. 2000, vol. 7, No. 3, pp. 263-286.

Carboni-Oerlemans et al., "Hydrolase-catalysed synthesis of peroxycarboxylic acids: Biocatalytic promiscuity for practical applications," Journal of Biotechnology, Nov. 2006, vol. 126, pp. 140-151.

Chen, J., "Enhanced Alkaline Peroxide Bleaching of Softwood Kraft Pulps Using a New Activator," Journal of Pulp and Paper Science, Dec. 2001, vol. 27, No. 12, 4 pages.

Chung, L., "Coordinative Binding of Divalent Cations with Ligands Related to Bacterial Spores," Biophysical Journal, Jun. 1971, vol. 11, pp. 469-482.

Dannacher, JJ., "Catalytic bleach: Most valuable applications for smart oxidation chemistry," Journal of Molecular Catalysis A: Chemical, May 2006, vol. 251, pp. 159-176.

(56) References Cited

OTHER PUBLICATIONS

Database CAPLUS Chemical Abstracts Service, Accession No. 1960:97225, abstract of DE 1024514, "Oxidation of Organic Compounds with Hydrogen Peroxide in the Liquid Base," Feb. 1958, 6 pages.

Effkemann et al., "Peroxide analysis in laundry detergents using liquid chromatography," Analytica chimica acta, May 1998, vol. 363, pp. 97-103.

Helrich, Kenneth, "A.O.A.C. Use Dilution Methods," Official Methods of Analysis of the Association of Official Analytical Chemists, 15th Edition, 1990, pp. 135-136.

Helrich, Kenneth, "Agricultural Chemicals; Contaminants; Drugs," Official Methods of Analysis of the Association of Official Analytical Chemists, 15th Edition, 1990, 11 pages.

Helrich, Kenneth, "Germicidal and Detergent Sanitizing Action of Disinfectants," Official Methods of Analysis of the Association of Official Analytical Chemists, 15th Edition, 1990, pp. 138-140.

Katz, Jonathan, "Report: Fracking to Grow U.S. Frack Water-Treatment Market Nine-Fold by 2020," Industry Week, May 2012, 2 pages.

Klaas et al., "Biocatalytic peroxy acid formation for disinfection," Journal of Molecular Catalysis B: Enzymatic, Dec. 2002, vol. 19-20, pp. 499-505.

Klaas et al., "Lipase-catalyzed conversions of trimethylsilyl ethers: deprotection, acetylation, epoxidation and one-pot-multi-step reactions," Journal of Molecular Catalysis B: Enzymatic, Dec. 1999, vol. 7, No. 5-6, pp. 283-289.

Klaas et al., "Lipase-catalyzed preparation of peroxy acids and their use for epoxidation," Journal of molecular catalysis A: Chemical, Mar. 1997, vol. 117, No. 1-3, pp. 311-319.

Lee et al., "Hydrolytic stability of a series of lactam-based cationic bleach activators and their impact on cellulose peroxide bleaching," Cellulose, Jun. 2010, vol. 17, pp. 671-678.

Leistner, L., "Basic aspects of good preservation by hurdle technology," International Journal of Food Microbiology, Apr. 2000, vol. 55, pp. 181-186.

Leistner, L., "Principles and applications for hurdle technology," in: G.W. Gould, New Methods of Food Preservation, 1995, 23 pages.

Leveneur et al., "Synthesis of peroxypropionic acid from propionic acid and hydrogen peroxide over heterogeneous catalysts," Chemical Engineering Journal, Apr. 2009, vol. 147, pp. 323-329.

Maeda et al., "Assessment of Acyl Groups and Reaction Conditions in the Competition between Perhydrolysis and Hydrolysis of Acyl Resorufins for Developing an Indicator Reaction for Fluorometric Analysis of Hydrogen Peroxide," Chemical and Pharmaceutical Bulletin, Feb. 2002, vol. 50, pp. 169-174.

Malow et al., "Prediction of the self-accelerating decomposition temperature (SADT) for liquid organic peroxides from differential scanning calorimetry (DSC) measurements," Journal of Hazardous Materials, Apr. 2005, vol. A120, pp. 21-24.

Muurinen, Esa, "Organosolv Pulping," Dissertation presented to the faculty of technology, University of Oulu, Finland, Jun. 30, 2000, 25 pages.

Nowack, Bernd, "Environmental chemistry of phosphates," Water Research, Jun. 2003, vol. 37, No. 11, pp. 2533-2546.

Ogata et al., "Radical Scavenging Activities of Niacin-Related Compounds," Bioscience, biotechnology, and biochemistry, Jan. 2002, vol. 66, No. 3, pp. 641-645.

Ogata et al., "The Formation of Peracids by the Perhydrolysis with Alkaline Hydrogen Peroxide," Tetrahedron, Jan. 1967, vol. 23, No. 8, pp. 3327-3332.

Popov et al., "Critical Evaluation of Stability Constants of Phosphonic Acids," Pure and Applied Chemistry, Oct. 2001, vol. 73, No. 10, pp. 1641-1677.

Rizkalla et al., "Metal Chelates of Phosphonate-Containing Ligands," Talanta, Sep. 1980, vol. 27, No. 9, pp. 715-719.

Suchy et al., "Improving Alkaline Peroxide Delignification Using a Vanadium Activator," Pulping Conference, Oct. 25-29, 1998, Book 3, 15 pages.

Swern, Daniel, "Organic Peroxides," Wiley-Interscience, 1970, vol. 1, 8 pages.

Tsunokawa et al., "A Versatile Method for Preparation of O-Alkylperoxycarbonic Acids: Epoxidation with Alkyloxycarbonylimidazoles and Hydrogen Peroxide," Tetrahedron Letters, 1982, vol. 23, No. 20, pp. 2113-2116.

United Nations, "Recommendations on the Transport of Dangerous Goods, Manual of Tests and Criteria," vol. 1, 17th revised edition, 2011, 200 pages.

Yin et al., "Switching catalysis from hydrolysis to perhydrolysis in P. fluorescens esterase," Biochemistry, Mar. 2010, vol. 49, No. 9, pp. 1931-1942.

\* cited by examiner

POLYMERIC AND SOLID-SUPPORTED CHELATORS FOR STABILIZATION OF PERACID-CONTAINING COMPOSITIONS

CROSS-REFERENCE TO RELATED APPLICATION

This application claims priority under 35 U.S.C. § 119 to Provisional Application U.S. Ser. No. 62/883,748, filed on Aug. 7, 2019, which is herein incorporated by reference in its entirety including without limitation, the specification, claims, and abstract, as well as any figures, tables, or examples thereof.

FIELD OF THE INVENTION

The present invention relates generally to methods of using a solid supported peracid stabilizer for peroxycarboxylic acids (also referred to as peracids) and peroxycarboxylic acid-containing compositions. In an embodiment, a solid supported peracid stabilizer is synthesized using chelator moiety(ies) and insoluble and inert polymers, such as synthesis of a dipicolinic acid-based polymeric chelating resin by installing dipicolinic acid moiety on a polystyrene resin backbone. In other embodiments, the solid support is non-polymeric. Beneficially, the solid supported stabilizers improve the stability of peroxycarboxylic acid-containing compositions and are suitable for use in stabilizing various sanitizing and disinfecting compositions, including sanitizing equipment to reduce yeasts, spores, bacteria and other contaminants in systems and on surfaces, including those having contact with food, food products and/or components thereof, which require or benefit from infection control suitable for direct contact with such food sources.

BACKGROUND INFORMATION

Peroxycarboxylic acid compositions are increasingly used as biocides in various fields owing to their broad biocidal efficacy and excellent environmental profiles. The most commonly used peroxycarboxylic acid is peracetic acid. Peracetic acid is a colorless, freely water-soluble liquid which has great biocidal efficacy toward various microorganisms, such as bacteria, virus, yeast, fungi and spores. When decomposed, peracetic acid results in acetic acid, water and oxygen. Pure peroxycarboxylic acids, such as peracetic acid, however, are unstable, and thus commercially available peroxycarboxylic acids are usually sold in an equilibrium solution and containing a stabilizing agent. These stabilizers act as efficient chelators of transition metal ions and prevent the decomposition of the peroxycarboxylic acids.

Various stabilizers are used in peroxycarboxylic acid compositions to stabilize the compositions. For example, pyridine carboxylic acid-based stabilizers, such as picolinic acid and salts, pyridine-2,6-dicarboxylic acid (DPA) and salts, and phosphonate based stabilizers, such as phosphoric acid and salts, pyrophosphoric acid and salts and most commonly 1-hydroxyethylidene-1,1-diphosphonic acid (HEDP) and salts, are used. When used individually at the right level, these stabilizers can significantly improve the stability of the peroxycarboxylic acid compositions, and for the conventional peroxycarboxylic acid compositions, the stability profile achieved with these stabilizers allows for the commercial use of these compositions. Other stabilizers are known for peroxide systems as well.

However, there remain disadvantages to use of many of these stabilizers. For example, the use of chemicals including stabilizers used in peracid compositions for food manufacturers—both direct and indirect food contact—are very strict with requirements for sanitizing compositions that are safe for food contact. In food, dairy, fermentation and beverage, and slaughterhouse facilities, there is an increased focus on food quality and environmental safety through avoiding undesired residues of any kind in products or waste streams. This includes residues from cleaning and sanitizing products in order to avoid having the residues remain on any food products and/or food surfaces when there is a non-rinse direct contact with food. In addition, in rinse applications it is desirable to eliminate residues as well, as they go through different waste-water treatment facilities on or off site, end up in surface water, or persist in the environment. Conventional stabilizers, including HEDP and DPA leave residues or residuals on treated surfaces. Accordingly, there is a demand and interest for use of stabilizers and other chemicals that do not impart residues onto the surfaces they treat, or even stabilizer-free compositions.

Although peroxycarboxylic acid compositions degrade into non-toxic, natural compounds, the stabilizers that are used in the chemical formulation of these products-such as etidronic acid and dipicolinic acid-impart the undesirable residues. For example, for both indirect or direct food or animal feed contact with stabilized peroxycarboxylic acid compositions (i.e. peroxyacetic acid) only very low usage limits are acceptable, which would not provide sufficient stabilization for the sanitizing and disinfecting composition. In addition, these conventional stabilizers fall outside of desired product categories like organic food additives. Moreover, the conventional stabilizers persist in animal bodies and the open environment.

As an additional limitation to the conventional stabilizers—such as etidronic acid and dipicolinic acid-they are expensive. Once the stabilizers have been dosed out with the product, they are not able to be recovered or re-used. Also, the phosphorous in etidronic acid causes issues with regulatory bodies trying to avoid hyper-fertilization of surface water. Accordingly, there are various needs for improved peroxycarboxylic acid composition stabilizers, in particular, stabilizers that are not solubilized chemical stabilizers (i.e. not in the bulk liquid product) yet provide the same mechanisms of stabilization for the peroxycarboxylic acid compositions.

Accordingly, it is an objective to develop stabilized peroxycarboxylic acid compositions that do not include stabilizers in the bulk liquid product.

It is an objective to provide solid supported stabilizers for peroxycarboxylic acid compositions, in particular polymers incorporating chelators for transition metals for peroxycarboxylic acid stabilizers.

Other objects, advantages and features of the present invention will become apparent from the following specification taken in conjunction with the accompanying drawings.

SUMMARY OF THE INVENTION

An advantage of the invention is to provide stable peroxycarboxylic acid compositions with solid supported stabilizers for stabilization and uses thereof. It is an advantage of the present invention that stable peroxycarboxylic acid compositions are suitable for contacting food surfaces or those involved in the manufacture of food sources while effectively cleaning and/or sanitizing without requiring a rinse step to remove chemicals used in the cleaning and/or sanitizing. Beneficially, the solid supported peracid stabilizers are not in the bulk liquid peroxycarboxylic acid composition and therefore do not result in residues on any treated surfaces.

In an embodiment, the use of a solid supported peracid stabilizer to stabilize a peroxycarboxylic acid composition comprises: providing a solid-supported peracid stabilizer to a peroxycarboxylic acid composition in need of stabilization, wherein the solid-supported peracid stabilizer comprises a chelant or chelant moiety(ies) linked to a solid support; wherein the peroxycarboxylic acid composition comprises a $C_1$-$C_{22}$ carboxylic acid, a $C_1$-$C_{22}$ percarboxylic acid, hydrogen peroxide, and water, and wherein the peroxycarboxylic acid composition retains at least about 80% of the peroxycarboxylic acid after 30 days storage at a temperature of at least 40° C. In some embodiments, the chelant or chelant moiety(ies) are covalently bonded to an insoluble and inert polymer solid support. In some embodiments, the polymer solid support comprises crosslinked or un-crosslinked polyalkylenes, polyacrylates, polycarbonate, polyarylenes, polyaryletherketones, polyamide-imides, or combinations thereof. In other embodiments, the polymer solid support comprises crosslinked polyethylene, polypropylene, polyalkylacrylates, polystyrene, polyurethane, polyvinyl chloride, polyphenol-aldehyde, polytetrafluoroethylene, polybutylene terephthalate, polycaprolactam, poly (acrylonitrile butadiene styrene), or combinations thereof. In a preferred embodiment, the polymer comprises polystyrene. In other embodiments, the chelant or chelant moiety(ies) are covalently bonded to an insoluble and inert non-polymeric solid support comprising biochar, carbon, amorphous carbon, activated carbon, silica, silica gel, clays, silicon carbide, zeolites, ceramics, or combinations thereof.

In some embodiments, the chelant or chelant moiety(ies) comprises a phosphonic acid, phosphate, phosphonate and/or salt, aminocarboxylic acid chelant, heterocyclic dicarboxylic acid, pyridine carboxylic acids, chelant moiety(ies) thereof, or combinations thereof. In some embodiments, the chelant or chelant moiety is 1-hydroxy ethylidene-1,1-diphosphonic acid (HEDP), pyridine-2,6-dicarboxylic acid, salts thereof, moiety(ies) thereof, or combinations thereof. In some embodiments, the solid supported peracid stabilizer is a dipicolinic acid-based polymeric chelating resin. In some embodiments, the solid supported peracid stabilizer is a solid resin added into a container of the peroxycarboxylic acid composition or applied as a coating to a surface of a container in contact with the peroxycarboxylic acid composition, wherein the containers house the peroxycarboxylic acid composition during storage and/or transport.

In additional embodiments, a stabilized peroxycarboxylic acid composition comprises: a $C_1$-$C_{22}$ carboxylic acid; a $C_1$-$C_{22}$ percarboxylic acid; hydrogen peroxide; and a solid supported peracid stabilizer comprising a chelant or chelant moiety(ies) linked to a polymeric or non-polymeric solid support. In embodiments, the composition is food safe and/or does not require a rinse step. In embodiments, the composition comprises from about 1 wt-% to about 80 wt-% of the $C_1$-$C_{22}$ carboxylic acid, from about 1 wt-% to about 40 wt-% of the $C_1$-$C_{22}$ peroxycarboxylic acid, from about 1 wt-% to about 80 wt-% of the hydrogen peroxide, and ≤1 wt-% of the stabilizer, or between about 0.1 wt-% to about 1 wt-% of the stabilizer, or between about 0.5 wt-% to about 1 wt-% of the stabilizer.

In additional embodiments, a method of method for reducing a microbial population using a stabilized peroxycarboxylic acid composition comprises: providing the peroxycarboxylic acid compositions; and contacting a surface or substrate with a use solution of said composition for sufficient time to reduce a microbial population, and wherein the stabilized peroxycarboxylic acid composition does not impart any residue from the solid supported peracid stabilizer onto the surface or substrate. In some embodiments, no rinse step is required and/or the composition is a food safe sanitizer. In some embodiments, the surface or substrate is a food item, plant item, animal item, a container, an equipment, a system or a facility for growing, fermentation equipment or surface, holding, processing, packaging, storing, transporting, preparing, cooking or serving the food item, plant item or the animal item, an instrument, a hard surface, a liquid media, equipment, a fouled water or industrial processing liquid source, liquid system, or process water used in oil, gas and/or industrial processing operations.

In some embodiments of the methods, the contacting step lasts for at least 10 seconds, or at least 15 seconds. In some embodiments, the microbial population in and/or on the surface or substrate is reduced by at least two log 10, or at least three log 10. In some embodiments, the contacting of the surface or substrate is by a spray, wipe, dip or submersion into the peroxycarboxylic acid composition, and/or wherein the surface or substrate is contacted with about 1 ppm to about 10,000 ppm of the peroxycarboxylic acid. In some embodiments, the peroxycarboxylic acid composition is diluted prior to the contacting.

In yet other embodiments, a method of synthesizing a polymeric/solid-supported chelating group or chelant moiety(ies) to stabilize a peroxycarboxylic acid composition comprises: (A) installing a chelating group or chelant moiety (ies) on a non-polymeric solid support and/or a preformed insoluble crosslinked polymeric material; (B) installing a chelating group or chelant moiety(ies) on a preformed insoluble crosslinked polymeric material; (C) forming a chelator functionalized polymerizable monomer followed by copolymerizing the chelator-functionalized polymerizable monomer with additional monomers and at least one crosslinking monomer; or (D) forming a chelator functionalized polymerizable monomer followed by copolymerizing the chelator-functionalized polymerizable monomer; wherein the chelating group or chelant moiety(ies) are insoluble in aqueous solvents and organic solvents.

In still other embodiments, a solid-supported peracid stabilizer composition comprises: a chelant or chelant moiety(ies) linked to a solid support, wherein the chelant or chelant moiety(ies) are linked via a covalent bond to the solid support that is either (A) an insoluble and inert polymer matrix or (B) an insoluble and inert non-polymeric matrix.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
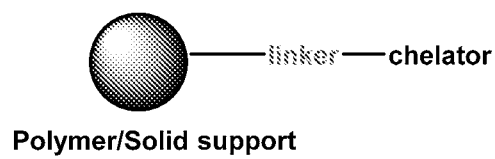
FIG. 1 shows a generalized representation of a peracid stabilizer that comprises a polymeric/solid peracid stabilizer supported on an insoluble and inert solid linked to a chelant (or chelant moiety(ies)).

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF INVENTION

The present invention relates to stabilized peroxycarboxylic acid compositions, solid-supported stabilizer, methods of producing the same, and methods of using the solid-supported stabilizers for stabilizing peroxycarboxylic acid compositions. The solid-supported peracid stabilizers have advantages over conventional stabilizers for peroxycarboxylic acids including elimination of chemical residues on treated surfaces, and water and other environmental impacts. The embodiments of this invention are not limited to particular compositions, methods of stabilizing and methods of use which can vary and are understood by skilled artisans. It is further to be understood that all terminology used herein is for the purpose of describing particular embodiments only and is not intended to be limiting in any manner or scope. For example, as used in this specification and the appended claims, the singular forms "a," "an" and "the" can include plural references unless the context clearly indicates otherwise. Further, all units, prefixes, and symbols may be denoted in their SI accepted form. Numeric ranges recited within the specification are inclusive of the numbers defining the range and include each integer within the defined range.

Numeric ranges recited within the specification are inclusive of the numbers within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5). Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation; the preferred materials and methods are described herein. In describing and claiming the embodiments of the present invention, the headings provided are not limitations on the embodiments of the invention and the following terminology will be used in accordance with the definitions set out below.

As used herein, the term "about" refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "cleaning," as used herein, means to perform or aid in soil removal, bleaching, microbial population reduction, or combination thereof. For the purpose of this patent application, successful microbial reduction is achieved when the microbial populations are reduced by at least about 50%, or by significantly more than is achieved by a wash with water. Larger reductions in microbial population provide greater levels of protection.

As used herein, "consisting essentially of" means that the methods and compositions may include additional steps, components, ingredients or the like, but only if the additional steps, components and/or ingredients do not materially alter the basic and novel characteristics of the claimed methods and compositions.

As used herein, the term "disinfectant" refers to an agent that kills all vegetative cells including most recognized pathogenic microorganisms, using the procedure described in A.O.A.C. Use Dilution Methods, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is affected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

As used herein, the term "free," "no," "substantially no" or "substantially free" refers to a composition, mixture, or ingredient that does not contain a particular compound or to which a particular compound or a particular compound-containing compound has not been added. Should the particular compound be present through contamination and/or use in a minimal amount of a composition, mixture, or ingredients, the amount of the compound shall be less than about 3 wt-%. More preferably, the amount of the compound is less than 2 wt-%, less than 1 wt-%, and most preferably the amount of the compound is less than 0.5 wt-% or 0.0 wt-%.

The term "hard surface" refers to a solid, substantially non-flexible surface such as a countertop, tile, floor, wall, panel, window, plumbing fixture, kitchen and bathroom furniture, appliance, engine, circuit board, and dish. Hard surfaces may include for example, health care surfaces and food/plant/animal processing surfaces.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the terms "mixed" or "mixture" when used relating to "percarboxylic acid composition," "percarboxylic acids," "peroxycarboxylic acid composition" or "peroxycarboxylic acids" refer to a composition or mixture including more than one percarboxylic acid or peroxycarboxylic acid.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

As used herein, the term "sulfoperoxycarboxylic acid," "sulfonated peracid," or "sulfonated peroxycarboxylic acid" refers to the peroxycarboxylic acid form of a sulfonated carboxylic acid. In some embodiments, the sulfonated peracids of the present invention are mid-chain sulfonated peracids. As used herein, the term "mid-chain sulfonated peracid" refers to a peracid compound that includes a sulfonate group attached to a carbon that is at least one carbon (e.g., the three position or further) from the carbon of the percarboxylic acid group in the carbon backbone of the percarboxylic acid chain, wherein the at least one carbon is not in the terminal position. As used herein, the term "terminal position," refers to the carbon on the carbon backbone chain of a percarboxylic acid that is furthest from the percarboxyl group.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition.

As used herein, the term "water" for treatment according to the invention includes a variety of sources, such as freshwater, pond water, sea water, saltwater or brine source, brackish water, recycled water, or the like. Waters are also understood to optionally include both fresh and recycled water sources (e.g. "produced waters"), as well as any combination of waters for treatment according to the invention. In some embodiments, produced water (or reuse water) refers to a mixture of water that comprises both water recycled from previous or concurrent oil- and gas-field operations, e.g., fracking, and water that has not been used in oil- and gas-field operations, e.g., fresh water, pond water, sea water, etc.

As used herein, "weight percent," "wt-%," "percent by weight," "% by weight," and variations thereof refer to the concentration of a substance as the weight of that substance divided by the total weight of the composition and multiplied by 100. It is understood that, as used here, "percent," "%," and the like are intended to be synonymous with "weight percent," "wt-%," etc.

It is understood that aspects and embodiments of the invention described herein include "consisting" and/or "consisting essentially of" aspects and embodiments. As used herein, "consisting essentially of" means that the methods and compositions may include additional steps, components, ingredients or the like, but only if the additional steps, components and/or ingredients do not materially alter the basic and novel characteristics of the claimed methods and compositions.

Stabilized Peroxycarboxylic Acid Compositions

Stabilized peroxycarboxylic acid compositions are provided. In an embodiment, the stabilized compositions include the exemplary ranges shown in Table 1A in weight percentage of the peroxycarboxylic acid-forming compositions and Table 1B in weight percentage of the peroxycarboxylic acid compositions.

Beneficially, the stabilized peroxycarboxylic acid compositions do not include additional stabilizing agents in the compositions. In such embodiments the polymeric (or non-polymeric) stabilizers are the only stabilizing agents and/or chelators included in the compositions. Examples of such additional stabilizing agents excluded from the compositions described herein, include for example, dipicolinic acid or 2,6-pyridinedicarboxylic acid (DPA), picolinic acid, or a salt thereof, phosphonate-based stabilizers such as phosphoric acid and salts, pyrophosphoric acid and salts and most commonly 1-hydroxyethylidene-1,1-diphosphonic acid (HEDP) and salts.

TABLE 1A

| Material | First Exemplary Range wt-% | Second Exemplary Range wt-% | Third Exemplary Range wt-% |
| --- | --- | --- | --- |
| Carboxylic Acid | 0.1-80 | 1-80 | 1-50 |
| Hydrogen Peroxide | 1-90 | 1-80 | 10-60 |
| Solvent (e.g. Water) | 1-75 | 1-60 | 1-20 |
| Polymeric/Solid-Supported Peracid Stabilizer | 0.01-10 | 0.01-5 | 0.1-2 |
| Mineral Acid | 0-10 | 0-8 | 0-5 |
| Additional Functional Ingredients | 0-25 | 0-20 | 0-10 |

TABLE 1B

| Material | First Exemplary Range wt-% | Second Exemplary Range wt-% | Third Exemplary Range wt-% |
|---|---|---|---|
| Peroxycarboxylic Acid | 5-40 | 5-30 | 5-20 |
| Carboxylic Acid | 1-80 | 1-50 | 10-40 |
| Hydrogen Peroxide | 1-80 | 1-50 | 10-50 |
| Solvent (e.g. Water) | 1-75 | 1-60 | 1-20 |
| Polymeric/Solid-Supported Peracid Stabilizer | 0.01-10 | 0.01-5 | 0.1-2 |
| Mineral Acid | 0-10 | 0-8 | 0-5 |
| Additional Functional Ingredients | 0-25 | 0-20 | 0-10 |

Polymeric Peracid Stabilizers

Polymeric peracid stabilizers for use in stabilizing peroxycarboxylic acid compositions are provided. As referred to herein, the polymeric peracid stabilizers are supported on an insoluble and inert solid instead of included in the bulk liquid peroxycarboxylic acid compositions. In an embodiment, the stabilizer is a chelant (or chelant moiety(ies)) covalently bonded to an insoluble and inert polymer solid support (i.e. matrix). Beneficially, a variety of chelant or chelant moiety(ies) can be synthesized with the solid supported polymer peracid stabilizer, as described herein, to allow the chelant to be in contact with the peroxycarboxylic acid without being in the bulk solution as a soluble component.

A generalized representation of a polymeric/solid-supported peracid stabilizer described herein is shown in FIG. 1 where the stabilizer comprises a polymeric/solid-supported peracid stabilizer on an insoluble and inert solid that is linked to a chelator (i.e. chelant or chelant moiety(ies)). As depicted in FIG. 1 either a polymeric or non-polymeric solid support can be provided as the insoluble and inert solid linked to the chelator (i.e. chelant or chelant moiety(ies)).

Figure 2:
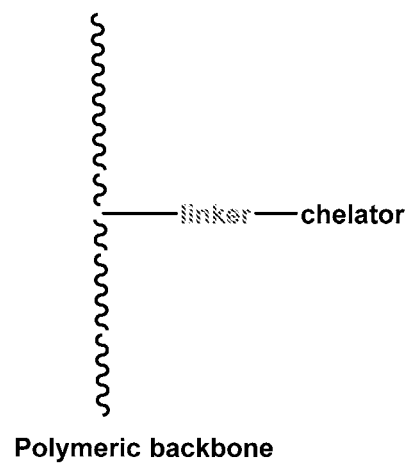
FIG. 2 shows a generalized representation of a peracid stabilizer that comprises a polymeric peracid stabilizer (i.e. chelator) supported on an insoluble and inert polymeric backbone.

A generalized representation of a polymeric peracid stabilizer described herein is shown in FIG. 2 where the stabilizer comprises a polymer backbone that is an insoluble and inert solid linked to a chelator (i.e. chelant or chelant moiety(ies)).

Chelants

As referred to herein, a chelant or chelant moiety(ies) is the stabilizer for the peroxycarboxylic acids. The term moiety refers to a part of a chelant molecule. As one skilled in the art understands a moiety describes a portion of the chelant molecule, such as those described herein, and is understood to refer to larger characteristic portions of the molecule as opposed to functional groups on the molecule.

Examples of suitable chelants include phosphates, phosphonates and/or salt(s), other metal chelating stabilizers (e.g. HEDP, NTA, DPA), aminocarboxylic acids (aminocarboxylic acid type sequestrant), and/or a heterocyclic dicarboxylic acid, e.g., dipicolinic acid. In some embodiments, the chelants are phosphonate based stabilizers, such as phosphoric acid and salts, pyrophosphoric acid and salts and most commonly 1-hydroxyethylidene-1,1-diphosphonic acid (HEDP) and salts.

Examples of phosphonic acids and phosphonate salts include, for example, 1-hydroxy ethylidene-1,1-diphosphonic acid (CH3C(PO3H2)2OH) (HEDP); ethylenediamine tetrakis methylenephosphonic acid (EDTMP); diethylenetriamine pentakis methylenephosphonic acid (DTPMP); cyclohexane-1,2-tetramethylene phosphonic acid; amino[tri(methylene phosphonic acid)]; (ethylene diamine[tetra methylene-phosphonic acid)]; 2-phosphene butane-1,2,4-tricarboxylic acid; or salts thereof, such as the alkali metal salts, ammonium salts, or alkyloyl amine salts, such as mono, di, or tetra-ethanolamine salts; or mixtures thereof. In certain embodiments, the chelants include 1-hydroxyethylidene-1, 1-diphosphonic acid (HEDP).

Examples of aminocarboxylic acid type chelants for use in the polymeric chelant stabilizers include, but are not limited to, the acids or alkali metal salts thereof, e.g., amino acetates and salts thereof. Suitable aminocarboxylates include, for example, N-hydroxyethylaminodiacetic acid; methylglycinediacetic acid (MGDA); hydroxyethylenediaminetetraacetic acid; nitrilotriacetic acid (NTA); ethylenediaminetetraacetic acid (EDTA); N-hydroxyethyl-ethylenediaminetriacetic acid (HEDTA); glutamic acid N,N-diacetic acid (GLDA), diethylenetriaminepentaacetic acid (DTPA); Iminodisuccinic acid (IDS); ethylenediamine disuccinic acid (EDDS); 3-hydroxy-2,2-iminodisuccinic acid (HIDS); hydroxyethyliminodiacetic acid (HEIDA); and alanine-N,N-diacetic acid; and the like; and mixtures thereof.

Further examples of suitable chelants include pyridine carboxylic acid based stabilizers, such as picolinic acid and salts, pyridine-2,6-dicarboxylic acid and salts having the following structure:

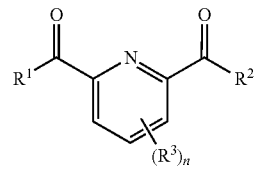

wherein $R^1$ is OH or $-NR^{1a}R^{1b}$, wherein $R^{1a}$ and $R^{1b}$ are independently hydrogen or $(C_1-C_6)$alkyl; $R^2$ is OH or $-NR^{2a}R^{2b}$, wherein $R^{2a}$ and $R^{2b}$ are independently hydrogen or $(C_1-C_6)$alkyl; each $R^3$ is independently $(C_1-C_6)$alkyl, $(C_2-C_6)$alkenyl or $(C_2-C_6)$alkynyl; and n is a number from zero to 3; or a salt thereof. Further suitable chelants have the structure:

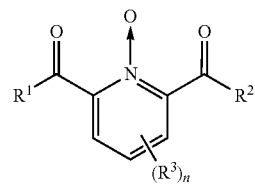

wherein $R^1$ is OH or $-NR^{1a}R^{1b}$, wherein $R^{1a}$ and $R^{1b}$ are independently hydrogen or $(C_1-C_6)$alkyl; $R^2$ is OH or $-NR^{2a}R^{2b}$, wherein $R^{2a}$ and $R^{2b}$ are independently hydrogen or $(C_1-C_6)$alkyl; each $R^3$ is independently $(C_1-C_6)$alkyl, $(C_2-C_6)$alkenyl or $(C_2-C_6)$alkynyl; and n is a number from zero to 3; or a salt thereof.

Further examples of suitable chelants include pyridine carboxylic acids having the following structure, which are isomer structures of 2,6pyridine (mono or di) carboxylic acids:

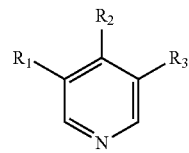

wherein $R_1$, $R_2$ and $R_3$ are independently COOH or H, or a salt thereof. In a further aspect, the pyridine carboxylic acid is a pyridine carboxylic acid oxide having the following structure:

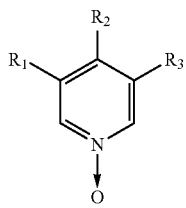

(I)

wherein $R_1$, $R_2$ and $R_3$ are independently COOH or H, or a salt thereof. Exemplary chelants include 3-pyridinecarboxylic acid (niacin, nicotinic acid, Vitamin B3), 4-pyridinecarboxylic acid (isonicotinic acid), 5-pyridinecarboxylic acid, 3,4-pyridinedicarboxylic acid, 3,5-pyridinedicarboxylic acid (dinicotinic acid), 4,5-pyridinedicarboxylic acid, 3,4,5-pyridinetricarboxylic acid, oxides thereof, and/or salts thereof.

Exemplary pyridine carboxylic acids can have the following structure:

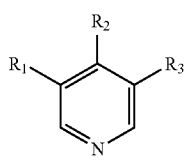

(I)

wherein $R_1$, $R_2$ and $R_3$ are independently COOH or H, or a salt thereof. Exemplary structures include the following structure:

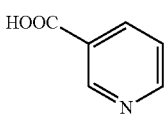

(Ia)

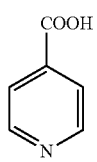

(Ib)

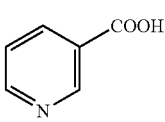

(Ic)

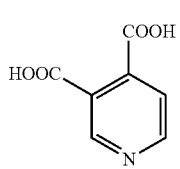

(Id)

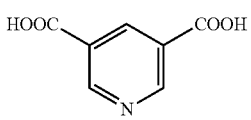

(Ie)

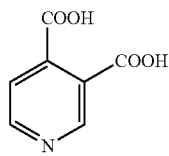

(If)

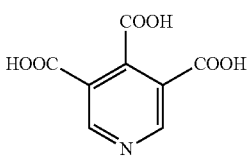

(Ig)

In a further aspect, the pyridine carboxylic acids can include pyridine carboxylic acid oxides having the following structure:

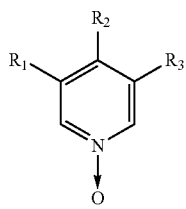

(II)

wherein $R_1$, $R_2$ and $R_3$ are independently COOH or H, or a salt thereof. Exemplary structures include the following structure:

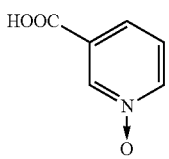

(IIa)

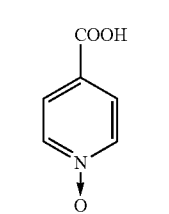

(IIb)

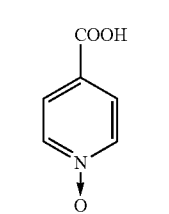

(IIc)

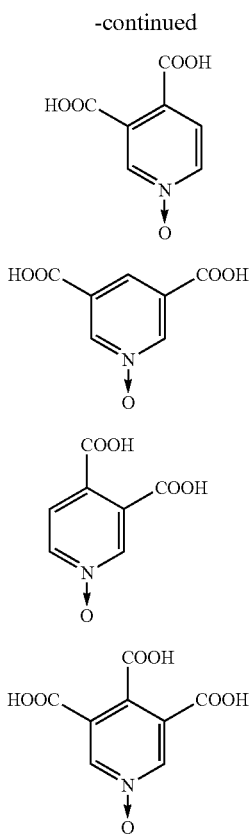

Polymeric Solid Support

The polymers provide the insoluble solid support for the peracid stabilizer. Any water-insoluble (solvent soluble), solid polymeric backbone that is inert to the peracid compositions and has functional groups to enable installation of chelator moieties can be used. The polymeric backbone can be crosslinked or un-crosslinked (i.e. solid polymers). Examples of suitable polymeric backbones include polyalkylenes, polyacrylates, polycarbonate, polyarylenes, polyaryletherketones, and polyamide-imides. In certain embodiments, the polymeric backbone is a crosslinked polyethylene, polypropylene, polyalkylacrylates, polystyrene, polyurethane, polyvinyl chloride, polyphenol-aldehyde, polytetrafluoroethylene, polybutylene terephthalate, polycaprolactam, and/or poly(acrylonitrile butadiene styrene).

The polymers provide the insoluble solid support for the peracid stabilizer. Any water-insoluble (solvent soluble), solid polymeric backbone that is inert to the peracid compositions and has functional groups to enable installation of chelator moieties can be used. The polymeric backbone can be crosslinked or un-crosslinked (i.e. solid polymers). Examples of suitable polymeric backbones include polyalkylenes, polyacrylates, polycarbonate, polyarylenes, polyaryletherketones, and polyamide-imides. In certain embodiments, the polymeric backbone is a polyethylene, polypropylene, polyalkylacrylates, polystyrene, polyurethane, polyvinyl chloride, polyphenol-aldehyde, polytetrafluoroethylene, polybutylene terephthalate, polycaprolactam, and/or poly(acrylonitrile butadiene styrene).

In still further embodiments, the polymeric backbone is a crosslinked polyethylene, polypropylene, polyalkylacrylates, polystyrene, polyurethane, polyvinyl chloride, polyphenol-aldehyde, polytetrafluoroethylene, polybutylene terephthalate, polycaprolactam, and/or poly(acrylonitrile butadiene styrene). In a preferred embodiment, the polymeric backbone is a vinyl polymer, such as polystyrene.

The polymeric peracid stabilizer comprising the chelant (or chelant moiety(ies)) are linked, such as by covalent bonding, to the polymeric backbone, which can be used at any suitable concentration in the peroxycarboxylic acid-forming composition or the peroxycarboxylic acid composition. In some embodiments, the stabilizer comprises from about 0.001 wt-% to about 10 wt-%, from about 0.01 wt-% to about 10 wt-%, from about 0.01 wt-% to about 5 wt-%, or from about 0.1 wt-% to about 2 wt-%. Without limiting the scope of invention, the numeric ranges are inclusive of the numbers defining the range and include each integer within the defined range.

Non-Polymeric Solid Support

In other embodiments, the peracid stabilizer can comprise a non-polymeric peracid stabilizers. As referred to herein, the non-polymeric peracid stabilizers are supported on an insoluble and inert solid instead of included in the bulk liquid peroxycarboxylic acid compositions. In an embodiment, the stabilizer is a chelant or chelant moiety(ies) covalently bonded to an insoluble and inert solid support or solid support (i.e. matrix). Exemplary non-polymeric solid supports include biochar, carbon, amorphous carbon, activated carbon, silica, silica gel, clays (e.g., kaolinite), silicon carbide, zeolites (e.g., mordenite), ceramics, and any combinations thereof. In one embodiment, the solid support is carbon. The support for carbon support can be biochar, amorphous carbon, and/or activated carbon. In another embodiment, the support is activated carbon.

A peracid stabilizer comprising the chelant (or chelant moiety(ies)) linked to a solid, non-polymeric backbone, can be used at any suitable concentration in the peroxycarboxylic acid-forming composition or the peroxycarboxylic acid composition. In some embodiments, the stabilizer comprises from about 0.001 wt-% to about 10 wt-%, from about 0.01 wt-% to about 10 wt-%, from about 0.01 wt-% to about 5 wt-%, or from about 0.1 wt-% to about 2 wt-%. Without limiting the scope of invention, the numeric ranges are inclusive of the numbers defining the range and include each integer within the defined range.

Beneficially, the solid support for the peracid stabilizer—both the polymeric solid support or the non-polymeric solid support—allows the stabilizer to be applied to containers or other surfaces in contact with the peroxycarboxylic acid composition in need of stabilization (e.g. interior surfaces of packaging, storage containers). The polymer/solid-supported materials are both inert to the peracid compositions and insoluble in both aqueous and organic solvents.

Peroxycarboxylic Acids

A peroxycarboxylic acid (i.e. peracid) is included for antimicrobial efficacy in the sanitizing compositions disclosed herein. As used herein, the term "peracid" may also be referred to as a "percarboxylic acid," "peroxycarboxylic acid" or "peroxyacid." Sulfoperoxycarboxylic acids, sulfonated peracids and sulfonated peroxycarboxylic acids are also included within the terms "peroxycarboxylic acid" and "peracid" as used herein. The terms "sulfoperoxycarboxylic acid," "sulfonated peracid," or "sulfonated peroxycarboxylic acid" refers to the peroxycarboxylic acid form of a sulfonated carboxylic acid as disclosed in, for example, U.S. Pat. Nos. 8,344,026, 8,809,392 and 9,359,295, each of which are incorporated herein by reference in their entirety. As one of skill in the art appreciates, a peracid refers to an acid having the hydrogen of the hydroxyl group in carboxylic acid replaced by a hydroxy group. Oxidizing peracids may also be referred to herein as peroxycarboxylic acids.

A peracid includes any compound of the formula R—(COOOH)n in which R can be hydrogen, alkyl, alkenyl, alkyne, acylic, alicyclic group, aryl, heteroaryl, or heterocyclic group, and n is 1, 2, or 3, and named by prefixing the parent acid with peroxy. Preferably R includes hydrogen, alkyl, or alkenyl. The terms "alkyl," "alkenyl," "alkyne," "acylic," "alicyclic group," "aryl," "heteroaryl," and "heterocyclic group" are as defined herein. As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups). Preferably, a straight or branched saturated aliphatic hydrocarbon chain having from 1 to 22 carbon atoms, such as, for example, methyl, ethyl, propyl, isopropyl (1-methylethyl), butyl, tert-butyl (1,1-dimethylethyl), and the like.

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

The term "alkenyl" includes an unsaturated aliphatic hydrocarbon chain having from 2 to 12 carbon atoms, such as, for example, ethenyl, 1-propenyl, 2-propenyl, 1-butenyl, 2-methyl-1-propenyl, and the like. The alkyl or alkenyl can be terminally substituted with a heteroatom, such as, for example, a nitrogen, sulfur, or oxygen atom, forming an aminoalkyl, oxyalkyl, or thioalkyl, for example, aminomethyl, thioethyl, oxypropyl, and the like. Similarly, the above alkyl or alkenyl can be interrupted in the chain by a heteroatom forming an alkylaminoalkyl, alkylthioalkyl, or alkoxyalkyl, for example, methylaminoethyl, ethylthiopropyl, methoxymethyl, and the like. Further, as used herein the term "alicyclic" includes any cyclic hydrocarbyl containing from 3 to 8 carbon atoms. Examples of suitable alicyclic groups include cyclopropanyl, cyclobutanyl, cyclopentanyl, etc. In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan. Additional examples of suitable heterocyclic groups include groups derived from tetrahydrofurans, furans, thiophenes, pyrrolidines, piperidines, pyridines, pyrrols, picoline, coumaline, etc.

According to the invention, alkyl, alkenyl, alicyclic groups, and heterocyclic groups can be unsubstituted or substituted by, for example, aryl, heteroaryl, C1-4 alkyl, C1-4 alkenyl, C1-4 alkoxy, amino, carboxy, halo, nitro, cyano, —SO3H, phosphono, or hydroxy. When alkyl, alkenyl, alicyclic group, or heterocyclic group is substituted, preferably the substitution is C1-4 alkyl, halo, nitro, amido, hydroxy, carboxy, sulpho, or phosphono. In one embodiment, R includes alkyl substituted with hydroxy. The term "aryl" includes aromatic hydrocarbyl, including fused aromatic rings, such as, for example, phenyl and naphthyl. The term "heteroaryl" includes heterocyclic aromatic derivatives having at least one heteroatom such as, for example, nitrogen, oxygen, phosphorus, or sulfur, and includes, for example, furyl, pyrrolyl, thienyl, oxazolyl, pyridyl, imidazolyl, thiazolyl, isoxazolyl, pyrazolyl, isothiazolyl, etc. The term "heteroaryl" also includes fused rings in which at least one ring is aromatic, such as, for example, indolyl, purinyl, benzofuryl, etc.

According to the invention, aryl and heteroaryl groups can be unsubstituted or substituted on the ring by, for example, aryl, heteroaryl, alkyl, alkenyl, alkoxy, amino, carboxy, halo, nitro, cyano, —SO3H, phosphono, or hydroxy. When aryl, aralkyl, or heteroaryl is substituted, preferably the substitution is C1-4 alkyl, halo, nitro, amido, hydroxy, carboxy, sulpho, or phosphono. In one embodiment, R includes aryl substituted with C1-4 alkyl.

Peracids suitable for use include any peroxycarboxylic acids, including varying lengths of peroxycarboxylic acids (e.g. C1-22) that can be prepared from the acid-catalyzed equilibrium reaction between a carboxylic acid described above and hydrogen peroxide. A peroxycarboxylic acid can also be prepared by the auto-oxidation of aldehydes or by the reaction of hydrogen peroxide with an acid chloride, acid anhydride, carboxylic acid anhydride, sodium alcoholate or alkyl and aryl esters. Alternatively, peracids can be prepared through non-equilibrium reactions, which may be generated for use in situ, such as the methods disclosed in U.S. Pat. Nos. 8,846,107 and 8,877,254, which are incorporated herein by reference in their entirety. Preferably a composition of the invention includes peroxyformic acid, peroxyacetic acid, peroxyoctanoic acid, peroxypropionic acid, peroxylactic acid, peroxyheptanoic acid, peroxyoctanoic acid and/or peroxynonanoic acid.

In some embodiments, a peroxycarboxylic acid includes at least one water-soluble peroxycarboxylic acid in which R includes alkyl of 1-22 carbon atoms. For example, in one embodiment, a peroxycarboxylic acid includes peroxyacetic acid. In another embodiment, a peroxycarboxylic acid has R that is an alkyl of 1-22 carbon atoms substituted with a hydroxyl group or other polar substituent such that the substituent improves the water solubility. Methods of preparing peroxyacetic acid are known to those of skill in the art including those disclosed in U.S. Pat. No. 2,833,813, which is herein incorporated herein by reference in its entirety.

In another embodiment, a sulfoperoxycarboxylic acid has the following structure:

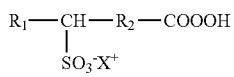

wherein R1 is hydrogen, or a substituted or unsubstituted alkyl group; R2 is a substituted or unsubstituted alkylene group; X is hydrogen, a cationic group, or an ester forming moiety; or salts or esters thereof. In some embodiments, R1 is a substituted or unsubstituted Cm alkyl group; X is hydrogen a cationic group, or an ester forming moiety; R2 is a substituted or unsubstituted Cn alkyl group; m=1 to 10; n=1 to 10; and m+n is less than 18, or salts, esters or mixtures thereof.

In some embodiments, R1 is hydrogen. In other embodiments, R1 is a substituted or unsubstituted alkyl group. In some embodiments, R1 is a substituted or unsubstituted alkyl group that does not include a cyclic alkyl group. In some embodiments, R1 is a substituted alkyl group. In some embodiments, R1 is an unsubstituted C1-C9 alkyl group. In some embodiments, R1 is an unsubstituted C7 or C8 alkyl. In other embodiments, R1 is a substituted C8-C10 alkylene group. In some embodiments, R1 is a substituted C8-C10 alkyl group is substituted with at least 1, or at least 2 hydroxyl groups. In still yet other embodiments, R1 is a substituted C1-C9 alkyl group. In some embodiments, R1 is a substituted C1-C9 substituted alkyl group is substituted with at least 1 SO3H group. In other embodiments, R1 is a C9-C10 substituted alkyl group. In some embodiments, R1 is a substituted C9-C10 alkyl group wherein at least two of the carbons on the carbon backbone form a heterocyclic group. In some embodiments, the heterocyclic group is an epoxide group.

In some embodiments, R2 is a substituted C1-C10 alkylene group. In some embodiments, R2 is a substituted C8-C10 alkylene. In some embodiments, R2 is an unsubstituted C6-C9 alkylene. In other embodiments, R2 is a C8-C10 alkylene group substituted with at least one hydroxyl group. In some embodiments, R2 is a C10 alkylene group substituted with at least two hydroxyl groups. In other embodiments, R2 is a C8 alkylene group substituted with at least one SO3H group. In some embodiments, R2 is a substituted C9 group, wherein at least two of the carbons on the carbon backbone form a heterocyclic group. In some embodiments, the heterocyclic group is an epoxide group. In some embodiments, R1 is a C8-C9 substituted or unsubstituted alkyl, and R2 is a C7-C8 substituted or unsubstituted alkylene.

In additional embodiments a sulfoperoxycarboxylic acid is combined with a single or mixed peroxycarboxylic acid composition, such as a sulfoperoxycarboxylic acid with peroxyacetic acid and peroxyoctanoic acid (PSOA/POOA/POAA). In other embodiments, a mixed peracid is employed, such as a peroxycarboxylic acid including at least one peroxycarboxylic acid of limited water solubility in which R includes alkyl of 5-22 carbon atoms and at least one water-soluble peroxycarboxylic acid in which R includes alkyl of 1-4 carbon atoms. For example, in one embodiment, a peroxycarboxylic acid includes peroxyacetic acid and at least one other peroxycarboxylic acid such as those named above. Preferably a composition of the invention includes peroxyacetic acid and peroxyoctanoic acid, such as disclosed in U.S. Pat. No. 5,314,687 which is herein incorporated by reference in its entirety. In an aspect, the peracid mixture is a hydrophilic peracetic acid and a hydrophobic peroctanoic acid, providing antimicrobial synergy. In an aspect, the synergy of a mixed peracid system allows the use of lower dosages of the peracids.

In another embodiment, a tertiary peracid mixture composition, such as peroxysulfonated oleic acid, peracetic acid and peroctanoic acid are employed, such as disclosed in U.S. Pat. No. 8,344,026 which is incorporated herein by reference in its entirety. Advantageously, a combination of peroxycarboxylic acids provides a composition with desirable antimicrobial activity in the presence of high organic soil loads. The mixed peroxycarboxylic acid compositions often provide synergistic micro efficacy. Accordingly, compositions of the invention can include a peroxycarboxylic acid, or mixtures thereof.

Various commercial formulations of peracids are available, including for example peracetic acid (approximately 15%) available as EnviroSan (Ecolab, Inc., St. Paul MN). Most commercial peracid solutions state a specific percarboxylic acid concentration without reference to the other chemical components in a use solution. However, it should be understood that commercial products, such as peracetic acid, will also contain the corresponding carboxylic acid (e.g. acetic acid), hydrogen peroxide and water.

In an aspect, any suitable C1-C22 peroxycarboxylic acid can be used in the present compositions. In some embodiments, the C1-C22 peroxycarboxylic acid is a C2-C20 peroxycarboxylic acid. In other embodiments, the C1-C22 peroxycarboxylic is a C1, C2, C3, C4, C5, C6, C7, C8, C9, C10, C11, C12, C13, C14, C15, C16, C17, C18, C19, C20, C21, or C22 carboxylic acid.

In an aspect of the invention, a peracid may be selected from a concentrated composition having a ratio of hydrogen peroxide to peracid from about 0:10 to about 10:0, preferably from about 0.5:10 to about 10:0.5, preferably from about 1:8 to 8:1. Various concentrated peracid compositions having the hydrogen peroxide to peracid ratios of about 0.5:10 to about 10:0.5, preferably from about 1:8 to 8:1, may be employed to produce a use solution for treatment according to the methods of the invention. In a further aspect of the invention, a peracid may have a ratio of hydrogen peroxide to peracid as low as from about 0.01 part hydrogen peroxide to about 1 part peracid. Without limiting the scope of invention, the numeric ranges are inclusive of the numbers defining the range and include each integer within the defined range.

Obtaining the preferred hydrogen peroxide to peroxycarboxylic acid ratios in a peracid composition may be obtained by a variety of methods suitable for producing a very low hydrogen peroxide to peracid ratio. In an aspect, equilibrium peracid compositions may be distilled to recover a very low hydrogen peroxide peracid mixture. In yet another aspect, catalysts for hydrogen peroxide decomposition may be combined with a peracid composition, including for example, peroxide-reducing agents and/or other biomimetic complexes. In yet another aspect, perhydrolysis of peracid precursors, such as esters and amides may be employed to obtain peracids with very low hydrogen peroxide.

In a preferred aspect, the C1-C22 peroxycarboxylic acid can be used at any suitable concentration. In some embodiments, the C1-C22 peroxycarboxylic acid has a concentration from about 0.1 wt-% to about 40 wt-% in a concentrated equilibrium composition. In other embodiments, the C1-C22 peroxycarboxylic acid has a concentration from about 1 wt-% to about 40 wt-%, or from about 1 wt-% to about 20 wt-%. In still other embodiments, the C1-C22 peroxycarboxylic acid has a concentration at about 1 wt-%, 2 wt-%, 3 wt-%, 4 wt-%, 5 wt-%, 6 wt-%, 7 wt-%, 8 wt-%, 9 wt-%, 10 wt-%, 11 wt-%, 12 wt-%, 13 wt-%, 14 wt-%, 15 wt-%, 16 wt-%, 17 wt-%, 18 wt-%, 19 wt-%, 20 wt-%, 25 wt-%, 30 wt-%, 35 wt-%, or 40 wt-%. Without limiting the scope of invention, the numeric ranges are inclusive of the numbers defining the range and include each integer within the defined range.

Carboxylic Acid

The peroxycarboxylic acid and peroxycarboxylic acid-forming compositions include a carboxylic acid. A carboxylic acid includes any compound of the formula R—(COOH)n in which R can be hydrogen, alkyl, alkenyl, alkyne, acylic, alicyclic group, aryl, heteroaryl, or heterocylic group, and n is 1, 2, or 3. Preferably R includes hydrogen, alkyl, or alkenyl. The terms "alkyl," "alkenyl," "alkyne," "acylic," "alicyclic group," "aryl," "heteroaryl," and "heterocyclic group" are as defined above with respect to peracids.

Examples of suitable carboxylic acids according to the equilibrium systems of peracids include a variety monocarboxylic acids, dicarboxylic acids, and tricarboxylic acids. Monocarboxylic acids include, for example, formic acid, acetic acid, propanoic acid, butanoic acid, pentanoic acid, hexanoic acid, heptanoic acid, octanoic acid, nonanoic acid, decanoic acid, undecanoic acid, dodecanoic acid, glycolic acid, lactic acid, salicylic acid, acetylsalicylic acid, mandelic acid, etc. Dicarboxylic acids include, for example, adipic acid, fumaric acid, glutaric acid, maleic acid, succinic acid, malic acid, tartaric acid, etc. Tricarboxylic acids include, for example, citric acid, trimellitic acid, isocitric acid, agaicic acid, etc.

In an aspect, a particularly well-suited carboxylic acid is water soluble such as formic acid, acetic acid, propionic acid, butanoic acid, lactic acid, glycolic acid, citric acid, mandelic acid, glutaric acid, maleic acid, malic acid, adipic acid, succinic acid, tartaric acid, etc. Preferably a composition of the invention includes acetic acid, octanoic acid, or propionic acid, lactic acid, heptanoic acid, octanoic acid, or nonanoic acid. Additional examples of suitable carboxylic acids are employed in sulfoperoxycarboxylic acid or sulfonated peracid systems.

Any suitable C1-C22 carboxylic acid can be used in the present compositions. In some embodiments, the C1-C22 carboxylic acid is a C2-C20 carboxylic acid. In other embodiments, the C1-C22 carboxylic acid is a C1, C2, C3, C4, C5, C6, C7, C8, C9, C10, C11, C12, C13, C14, C15, C16, C17, C18, C19, C20, C21, or C22 carboxylic acid.

The C1-C22 carboxylic acid can be used at any suitable concentration. In some embodiments, the C1-C22 carboxylic acid has a concentration in an equilibrium composition from about 0.1 wt-% to about 80 wt-%. In other embodiments, the C1-C22 carboxylic acid has a concentration from about 1 wt-% to about 80 wt-%. In still other embodiments, the C1-C22 carboxylic acid has a concentration at about 1 wt-% to about 50 wt-%. Without limiting the scope of invention, the numeric ranges are inclusive of the numbers defining the range and include each integer within the defined range.

Hydrogen Peroxide

The peroxycarboxylic acid and peroxycarboxylic acid-forming compositions include hydrogen peroxide. Hydrogen peroxide, $H_2O_2$, provides the advantages of having a high ratio of active oxygen because of its low molecular weight (34.014 g/mole) and being compatible with numerous substances that can be treated by methods of the invention because it is a weakly acidic, clear, and colorless liquid. Another advantage of hydrogen peroxide is that it decomposes into water and oxygen. It is advantageous to have these decomposition products because they are generally compatible with substances being treated. For example, the decomposition products are generally compatible with metallic substance (e.g., substantially noncorrosive) and are generally innocuous to incidental contact and are environmentally friendly.

In an embodiment, hydrogen peroxide is initially in an antimicrobial peracid composition in an amount effective for maintaining an equilibrium between a carboxylic acid, hydrogen peroxide, and a peracid. The amount of hydrogen peroxide should not exceed an amount that would adversely affect the antimicrobial activity of a composition of the invention. In further aspects of the invention, hydrogen peroxide concentration can be significantly reduced within an antimicrobial peracid composition. In some aspects, an advantage of minimizing the concentration of hydrogen peroxide is that antimicrobial activity of a composition of the invention is improved as compared to conventional equilibrium peracid compositions.

The hydrogen peroxide can be used at any suitable concentration. In some embodiments, a concentrated equilibrium composition has a concentration of hydrogen peroxide from about 0.5 wt-% to about 90 wt-%, or from about 1 wt-% to about 90 wt-%. In still other embodiments, the hydrogen peroxide has a concentration from about 1 wt-% to about 80 wt-%, from about 1 wt-% to about 60 wt-%, from about 10 wt-% to about 60 wt-%, or from about 1 wt-% to about 50 wt-%. Without limiting the scope of invention, the numeric ranges are inclusive of the numbers defining the range and include each integer within the defined range. Beneficially, the compositions and methods of the invention in providing stabilized equilibrium peracid compositions, are not reliant and/or limited according to any particular ratio of hydrogen peroxide to peracid for such enhanced stability.

Water

The peroxycarboxylic acid and peroxycarboxylic acid-forming compositions include water as a solvent. Water can be used at any suitable concentration. In some embodiments, a concentrated equilibrium composition has a concentration of water from about 0.01 wt-% to about 50 wt-%, from about 0.1 wt-% to about 50 wt-%, or from about 1 wt-% to about 10 wt-%. Without limiting the scope of invention, the numeric ranges are inclusive of the numbers defining the range and include each integer within the defined range.

Mineral Acid

In some embodiments, the peroxycarboxylic acid and peroxycarboxylic acid-forming compositions include a mineral acid. In some embodiments, the peracid composition has a use solution pH of 4 or less, and preferably has a use solution pH of 3 or less. In some embodiments, the present composition includes an inorganic acid. In preferred embodiments, the present composition includes a mineral acid. Particularly suitable mineral acids include sulfuric acid ($H_2SO_4$), sodium hydrogen sulfate, nitric acid, sulfamic acid and sulfonic acids both alkyl and aryl, in particular methane sulfonic acid and dodecylbenzene, toluene, xylene, naphthalene and cumene sulfonic acid, and/or phosphoric acid ($H_3PO_4$).

In a further aspect, the acids suitable for use include are not limited to mineral acids. Instead, acids suitable for use include strong acids, which are defined as those with a pKa near or below the lower pKas of HEDP which may cause significant protonation of the HEDP and other phosphate and phosphonate stabilizers and thus diminish their ability to stabilize the peracid chemistries. Additional description of mineral acids for use in peracid compositions is disclosed in WO 91/07375, which is herein incorporated by reference in its entirety.

The mineral acid providing the strong acidity of the peracid compositions can be used at any suitable concentration. In some embodiments, the mineral acid is a catalyst for the peroxycarboxylic acid reaction. In other embodiments, the mineral acid is an acidulant for the formed peroxycarboxylic acid composition. In some embodiments, a concentrated equilibrium composition has a concentration of the mineral acid from about 0.1 wt-% to about 50 wt-%, or from about 0.5 wt-% to about 50 wt-%. In still other embodiments, the mineral acid has a concentration from about 0.5 wt-% to about 20 wt-%, or more preferably from about 0.5 wt-% to about 10 wt-%. Without limiting the scope of invention, the numeric ranges are inclusive of the numbers defining the range and include each integer within the defined range.

Additional Functional Ingredients

In some embodiments, the peroxycarboxylic acid compositions can further comprise additional functional ingredients. In some embodiments, the peracid compositions including the solid supported peracid stabilizer, peroxycarboxylic acid, carboxylic acid, hydrogen peroxide and water make up a large amount, or even substantially all of the total weight of the compositions. For example, in some embodiments few or no additional functional ingredients are disposed therein.

In other embodiments, mineral acids, and/or additional functional ingredients may be included in the compositions. The functional ingredients provide desired properties and functionalities to the compositions. For the purpose of this application, the term "functional ingredient" includes a material that when dispersed or dissolved in a use and/or concentrate solution, such as an aqueous solution, provides a beneficial property in a particular use. Some particular examples of functional materials are discussed in more detail below, although the particular materials discussed are given by way of example only, and that a broad variety of other functional ingredients may be used. In some aspects, the compositions may include defoaming agents, surfactants, fluorescent tracer molecules, additional antimicrobial agents, enzymes, anti-redeposition agents, bleaching agents, solubility modifiers, viscosity enhancers, dispersants, rinse aids, metal protecting agents, corrosion inhibitors, scale inhibitors, fragrances and/or dyes, rheology modifiers or thickeners, hydrotropes or couplers, buffers, solvents and the like.

The additional functional ingredients can be used at any suitable concentration. In some embodiments, additional functional ingredients have a concentration from about 0 wt-% to about 25 wt-%, or from about 0 wt-% to about 20 wt-%. In still other embodiments, the additional functional ingredients have a concentration from about 0.01 wt-% to about 5 wt-%, from about 0.05 wt-% to about 5 wt-%, from about 0.1 wt-% to about 2 wt-%, or more preferably from about 0.5 wt-% to about 2 wt-%. Without limiting the scope of invention, the numeric ranges are inclusive of the numbers defining the range and include each integer within the defined range.

Methods of Synthesizing Polymer/Solid-Supported Peracid Stabilizers

The polymeric/solid-supported peracid stabilizers depicted in FIGS. 1-2 can be synthesized according to one of two general pathways. The polymeric/solid-supported peracid stabilizers provide chelating group-containing polymeric materials that are insoluble in both aqueous and organic solvents. In a first general embodiment, the peracid stabilizer is made by adding a chelant to a polymeric backbone. In a second general embodiment, the peracid stabilizer is made by selecting monomers to provide polymer moiety(ies) and combining with chelants. Further detail of the embodiments of synthesis are provided herein and depicted using exemplary embodiments in FIGS. 3-6.

Figure 3:
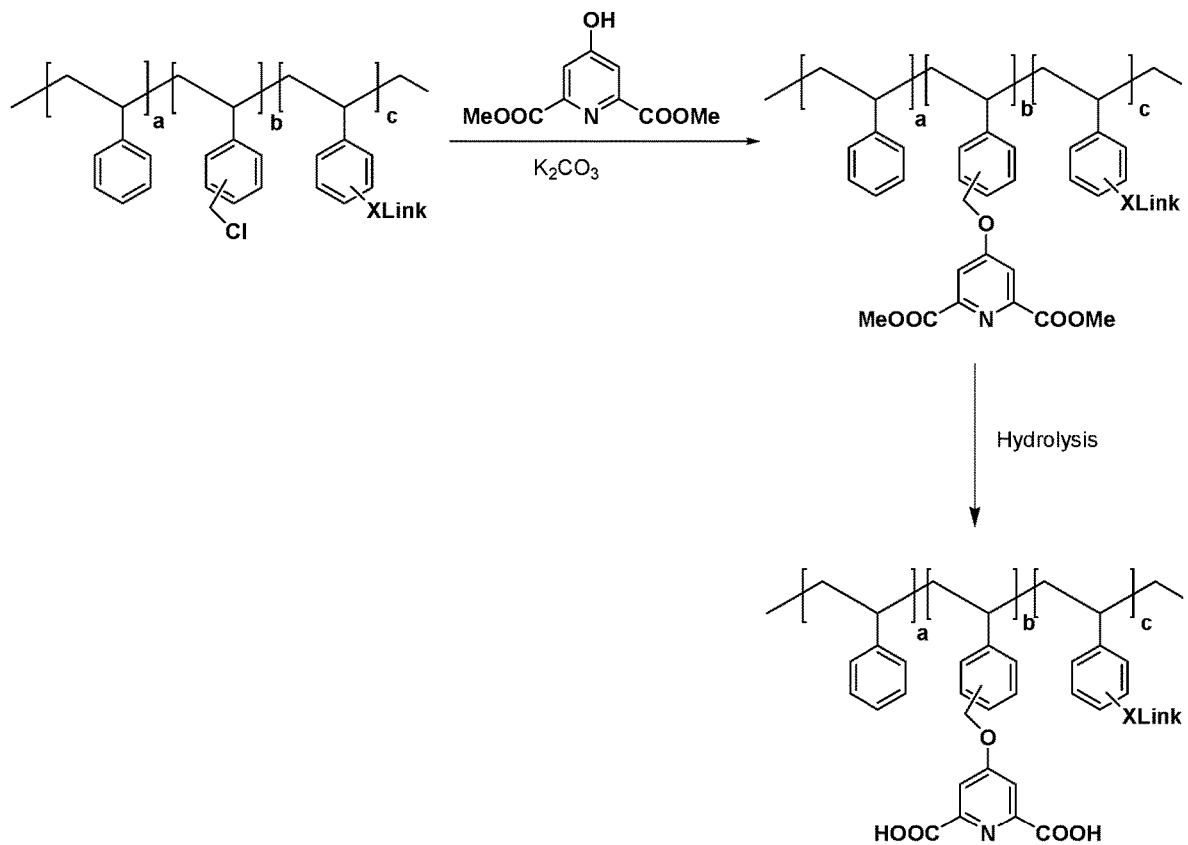
FIG. 3 shows a reaction pathway for the production of dipicolinic acid functionalized polystyrene resin, a solid-supported stabilizer, as described in Example 1.

In an embodiment, a route to synthesize polymeric/solid-supported peracid stabilizers is based on installing chelating moiety on the non-polymeric solid support and preformed/existing insoluble/crosslinked polymeric material (such as crosslinked polystyrene resin). An exemplary synthesis scheme is shown in FIG. 3. FIG. 3 shows an exemplary reaction to prepare of DPA functionalized-polystyrene based chelator by installing DPA on the chloromethylated crosslinked polystyrene resin beads.

Figure 4A:
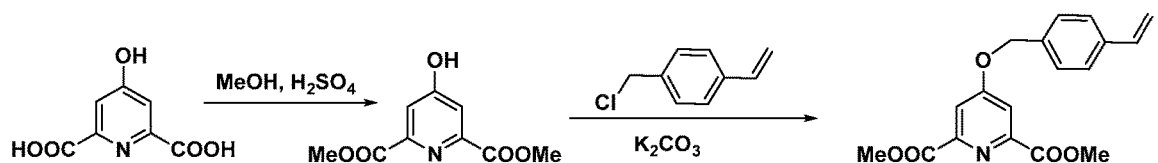
FIGS. 4A-4B shows a reaction pathway for forming a chelator functionalized polymerizable monomer (FIG. 4A) followed by the copolymerization of chelator-functionalized polymerizable monomer with other monomers such as styrene and at least one crosslinking monomer (FIG. 4B).
Figure 4B:
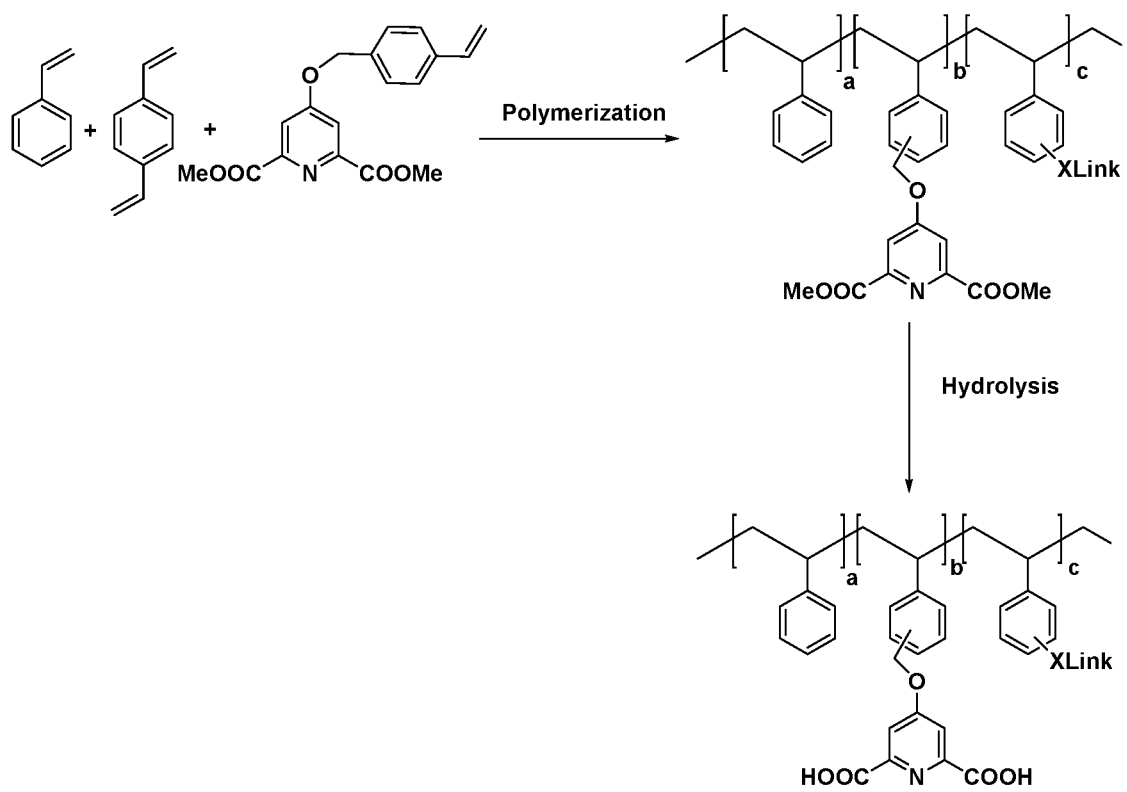

In another embodiment, a route to synthesize polymeric/solid-supported peracid stabilizers is based on forming a chelator functionalized polymerizable monomer followed by the copolymerization of chelator-functionalized polymerizable monomer with other monomers such as styrene and at least one crosslinking monomer. An exemplary synthesis scheme is shown in FIGS. 4A-4B. FIGS. 4A-4B show an exemplary reaction to prepare DPA functionalized monomer followed by ter-polymerization of chelator-functionalized polymerizable monomer styrene and divinylbenzene. FIG. 4A shows the steps to synthesize DPA functionalized monomer, and FIG. 4B shows copolymerization of DPA-functionalized polymerizable monomer with other monomers to yield insoluble chelating crosslinked polymer.

Figure 5:
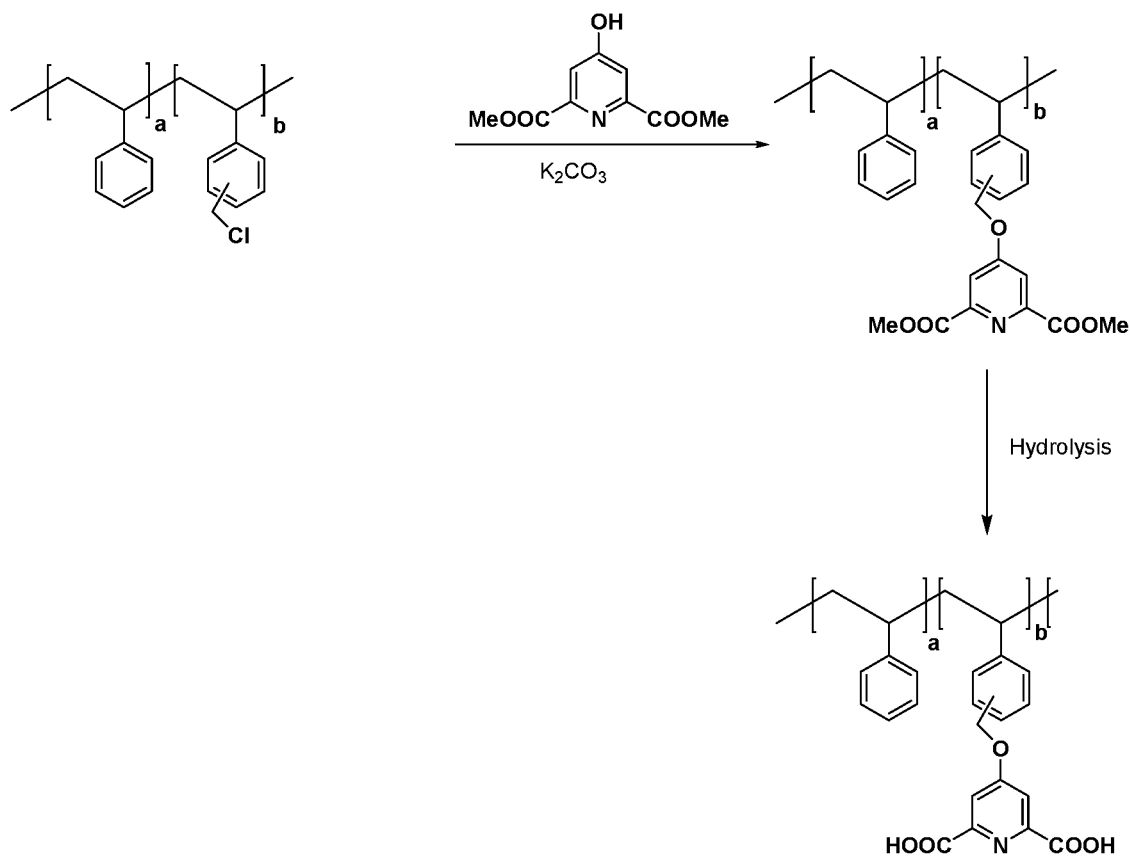
FIG. 5 shows a reaction pathway for the production of dipicolinic acid (DPA) functionalized polystyrene chelator by installing DPA on the polymeric backbone (i.e. chloromethylated polystyrene).

In still further embodiments for polymeric chelators for peracid stabilization, there are two synthesis routes. In a first embodiment, the chelating group-containing polymeric materials is produced by installing chelating moiety on the preformed/existing polymeric material as shown in FIG. 5. FIG. 5 depicts an exemplary reaction to prepare of DPA functionalized-polystyrene based chelator by installing DPA on the chloromethylated polystyrene.

Figure 6A:
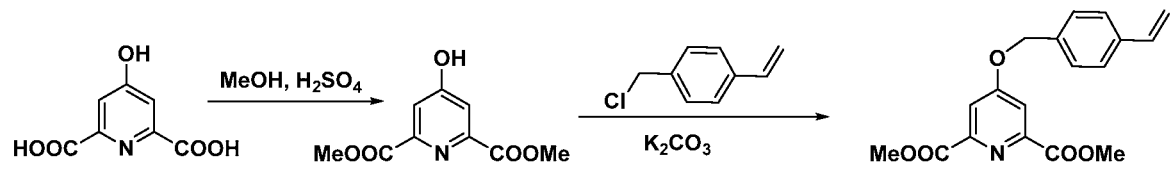
FIGS. 6A-6B shows a reaction pathway for forming a chelator functionalized polymerizable monomer (FIG. 6A) followed by the copolymerization of chelator-functionalized polymerizable monomer with other monomers such as styrene (without an additional crosslinking monomer) (FIG. 6B).
Figure 6B:
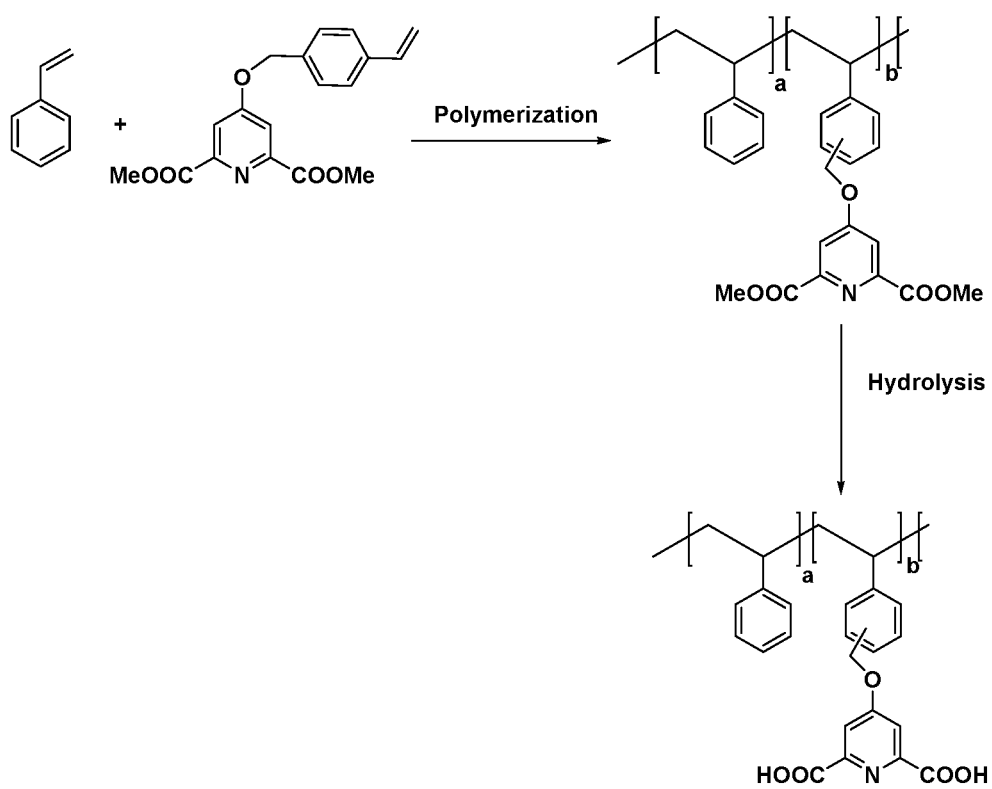

In a second embodiment, the chelating group-containing polymeric materials is produced by forming a chelator functionalized polymerizable monomer followed by the copolymerization of the chelator-functionalized polymerizable monomer with other monomers, such as styrene as shown in FIGS. 6A-6B. FIG. 6A shows an exemplary reaction to prepare DPA functionalized monomers and FIG. 6B shows the co-polymerization of chelator-functionalized polymerizable monomer styrene, specifically the copolymerization of DPA-functionalized polymerizable monomer with styrene to yield organic-solvent soluble chelating polymer.

As described herein, the cross-linking used is a covalent bonding in the various synthesis schemes. In embodiments, the linkages can include for example, esters, amides, sulfonoamides, ether, carbonyl, sulfide (thio-ether), azo, alkylene, arylene, carbamate, carbonate, and the like. These are non-limiting examples of the linkages suitable for use as described herein.

Methods of Using the Polymeric/Solid-Supported Peracid Stabilizers

The polymeric/solid-supported peracid stabilizers are suitable for use in any peroxycarboxylic acid compositions to maintain stability of the composition. The stabilized peroxycarboxylic acid compositions are suitable for storing, transporting and/or applying for treatment a stabilized peroxycarboxylic acid composition. In an embodiment, at least about 80% of the peroxycarboxylic acid is retained in the composition after storage for any suitable time under any suitable conditions, e.g., retaining at least about 80% of the peroxycarboxylic acid after storage of about 30 days at about 40° C. or above. Preferably, the methods include retaining at least about 85%, at least about 90%, or at least about 95% or higher of the peroxycarboxylic acid in the composition after storage of about 30 days at about 40° C. or above. As referred to herein, peroxycarboxylic acid content or peroxycarboxylic acid in the composition is measured by idiometric titration for the presence of a defined minimal amount of peroxycarboxylic acid in the composition after the 30 days storage at the identified temperature.

In an embodiment, the polymeric/solid-supported peracid stabilizer can be added into a container (i.e. submersed therein) as a solid resin, such as beads or strands. In an embodiment the beads or strands are porous. The container can include any type of reservoir or other housing that stores and/or dispenses the peroxycarboxylic acid composition, such as during storage and/or transport.

In an embodiment, the solid resin, such as beads or strands can be recycled and regenerated. The polymeric/solid-supported peracid stabilizer described herein may be recycled. Thus, in one aspect, provided herein are methods of producing compositions using recyclable polymeric/solid-supported peracid stabilizers. Any method known in the art may be used to separate the polymeric/solid-supported peracid stabilizer for reuse, including, for example, centrifugation, filtration (e.g., vacuum filtration), and gravity settling. In some of embodiments wherein at least a portion of the polymeric/solid-supported peracid stabilizer is recycled, it is recycled at least 1, at least 2, at least 3, at least 4, at least 5, at least 6, at least 7, at least 8, at least 9 or at least 10 times. In some of these embodiments, the polymeric/solid-supported peracid stabilizer retains at least 80%, at least 90%, at least 95%, at least 96%, at least 97%, at least 98%, or at least 99% activity after being recycled 1, 2, 3, 4, 5, 6, 7, 8, 9 or 10 times, when compared to the polymeric/solid-supported peracid stabilizer activity under identical conditions prior to being recycled.

In such embodiments, the recycled polymeric/solid-supported peracid stabilizer has a measurable lifetime. As used herein "the polymeric/solid-supported peracid stabilizer lifetime" refers to the average number of cycles that it can be re-used before it no longer effectively chelates the metal. The polymeric/solid-supported peracid stabilizer lifetime is calculated as the reciprocal of the loss of activity. For example, if the loss of activity is 1% per cycle, then the polymeric/solid-supported peracid stabilizer lifetime is 100 cycles. In some variations, the lifetime is at least 1 cycle, at least 2 cycles, at least 10 cycles, at least 50 cycles, at least 100 cycles, at least 200 cycles, at least 500 cycles.

In another embodiment, the polymeric peracid stabilizer is applied as a coating to a surface in contact with the peroxycarboxylic acid composition. The use of the polymeric peracid stabilizer in a coating applied to a surface can vary depending upon the substrate surface to be coated as well as the type of polymer material used in the stabilizer system. In some embodiments of a coating with the polymeric peracid stabilizer, physical adsorption of polymer onto a surface (i.e. direct deposition) can be achieved either with or without a solvent (and optionally with additional components such as pigments, etc.) added to the formulation that aid in affixing polymeric material to the surface to be coated. In an embodiment, the coating of the polymeric peracid stabilizer once cured or dried provides a film of the polymeric peracid stabilizer. In some embodiments the film is a thin opaque film. In some embodiments, the thin film can be further decorative (e.g. inclusion of pigments). Beneficially, the film coating ensure the contacting of the peroxycarboxylic acid composition to the polymeric peracid stabilizer. Additional description of use of polymers for surface coatings is set forth in Britannica Technology-Surface Coating (https://www.britannica.com/technology/surface-coating) and additional description of methods for coating surfaces are disclosed by Kumar et al. in "Fabrication Methods of Organic/Inorganic Nanocomposite Coatings," Polymer Coatings: Technology and Applications, 21-40, 2020, each of which are herein incorporated by reference in its entirety.

In embodiments where a surface is coated with the polymeric peracid stabilizer, the surface can include for example, the interior surface (i.e. walls) of a container, reservoir or other housing that stores and/or dispenses the peroxycarboxylic acid composition, such as during storage and/or transport. In a still further embodiment, the surface in contact with the peroxycarboxylic acid composition can include dispensing tubing, or specifically the surface of the dispensing tubing.

In a still further embodiment, the polymeric/solid-supported peracid stabilizer is contained in a porous material, such as pouch, envelope or other container that is made of a material capable of retaining the solids (e.g., beads or strands) while being permeable to the peroxycarboxylic acid composition. In such an embodiment, the polymeric/solid-supported peracid stabilizer contained in the pouch, envelope or other container can be added into a container (i.e. submersed therein). The container can include any type of reservoir or other housing that stores and/or dispenses the peroxycarboxylic acid composition, such as during storage and/or transport.

In exemplary embodiments the pouch, envelope or other container can be made of any porous water-insoluble polymeric materials. The porous polymer is any suitable porous polymer, but is, preferably, is a polysulfone (PS), polyethylene (PE), polystyrene divinylbenzene copolymers, polyacrilonitrile (PAN), polyethersulfone (PES), polyetherimide (PEI), poly(amide-imide) (PAI), polyvinylidene difluoride (PVDF), polyvinylidene fluoride (PVDF), polydimethylsiloxane (PDMS), poly(3-octylthiophene) (POT), poly (3-(2-acetoxyethylthiophene) (PAET), polyimide, polyamide, polyetheretherketones (PEEK), and poly(vinyl acetate) (PVAc), polypropylene, cellulose acetate, 2,2-bis(3,4-carboxyphenyl) hexafluoropropane dianhydride-diaminomesitylene) (6FDA-DAM), and/or derivatives or combinations thereof. Additional examples of polymeric materials are disclosed in Michael S. Silverstein et al., Porous Polymers, John Wiley & Sons, Inc., 2011, Hypercrosslinked porous polymer materials: design, synthesis, and applications, Chem. Soc. Rev., 2017, 46, 3322-3356, Porous Polymers as Multifunctional Material Platforms toward Task-Specific Applications, Advanced Materials, 2019, 31(4), and J. of Nanomaterials, Volume 2015, Article ID 142195, each of which are herein incorporated by reference in its entirety.

Beneficially, the peroxycarboxylic acid composition can be stored and/or transported while in contact with the solid supported polymeric peracid stabilizer without the solid being dispensed with the peroxycarboxylic acid composition. Accordingly, the polymeric/solid-supported peracid stabilizer does not come into contact with the treated surface and/or substrate. This in effect provides a stable peroxycarboxylic acid composition that does not include solubilized stabilizers.

In embodiments, the polymeric/solid-supported peracid stabilizers can be used for an extended period of time, from a few months to a few years (as referred to as the 'lifetime' as described above). In certain embodiments, the solid supported polymeric peracid stabilizers may become exhausted through the chelation of transition metal ions and may require regeneration for re-use (i.e. recycle as described above), such as through the use of a strong acid. However, in other embodiments, an exhausted polymeric/solid-supported peracid stabilizer can be disposed.

Methods of Using the Stabilized Peroxycarboxylic Acid Compositions

In an embodiment, the stabilized compositions are used for sanitizing surfaces, targets and/or products. The compositions are particularly suitable for use as a hard surface sanitizer and/or disinfectant, a CIP sanitizer, food and/or tissue treatment sanitizer, an environmental disinfectant, a laundry bleach and disinfectant, and/or an indirect food contact sanitizer. The present methods can be used in the methods, processes or procedures described and/or claimed in U.S. Pat. Nos. 5,200,189, 5,314,687, 5,718,910, 6,165,483, 6,238,685B1, 8,017,409 and 8,236,573, each of which are herein incorporated by reference in their entirety.

The compositions are particularly suitable for direct or indirect contact sanitizer for a food item or a plant item and/or at least a portion of a medium, a container, an equipment, a system or a facility for growing, holding, processing, packaging, storing, transporting, preparing, cooking or serving the food item or the plant item. The present methods can be used for treating any suitable plant item. In some embodiments, the plant item is a grain, fruit, vegetable or flower plant item, a living plant item or a harvested plant item. In addition, the present methods can be used for treating any suitable food item, e.g., an animal product, an animal carcass or an egg, a fruit item, a vegetable item, or a grain item. In still other embodiments, the food item may include a fruit, grain and/or vegetable item.

The present methods can be used for treating a target that is at least a portion of a container, an equipment, a system or a facility for holding, processing, packaging, storing, transporting, preparing, cooking or serving the food item or the plant item. In some embodiments, the target is at least a portion of a container, an equipment, a system or a facility for holding, processing, packaging, storing, transporting, preparing, cooking or serving a meat item, a fruit item, a vegetable item, or a grain item. In other embodiments, the target is at least a portion of a container, an equipment, a system or a facility for holding, processing, packaging, storing, or transporting an animal carcass. In still other embodiments, the target is at least a portion of a container, an equipment, a system or a facility used in food processing, food service or health care industry. In yet other embodiments, the target is at least a portion of a fixed in-place process facility. An exemplary fixed in-place process facility can comprise a milk line dairy, a continuous brewing system, a pumpable food system or a beverage processing line.

The present methods are particularly well suited for treating and sanitizing equipment, such as fermentation equipment which are vulnerable to yeasts, spores and bacteria in the systems and within a mash source generated. This presents unique challenges requiring antimicrobial and sanitizing methods that come into direct contact with feed sources, namely animal feed. Accordingly, there is a unique benefit of providing the stabilized peroxycarboxylic acid compositions having food-safe stabilizers employed therein, as the solid supported peracid stabilizer s to not leave any residues on treated surfaces. Beneficially, the stabilized peroxycarboxylic acid compositions can be used to sanitize a surface without the need to rinse the surfaces thereafter.

The present methods can be used for treating a target that is at least a portion of a solid surface or liquid media. In some embodiments, the solid surface is an inanimate solid surface. The inanimate solid surface can be contaminated by a biological fluid, e.g., a biological fluid comprising blood, other hazardous body fluid, or a mixture thereof. In other embodiments, the solid surface can be a contaminated surface. An exemplary contaminated surface can comprise the surface of food service wares or equipment, or the surface of a fabric.

The various methods of treatment can include the use of any suitable level of the peroxycarboxylic acid. In some embodiments, the treated target composition comprises from about 1 ppm to about 10,000 ppm, about 10 ppm to about 1,000 ppm, or any ranges therebetween, of the peroxycarboxylic acid, including any of the peroxycarboxylic acid compositions according to the invention.

In still another aspect, the stabilized peroxycarboxylic acid compositions can be used in water treatment methods and other industrial processes uses of the compositions for sanitizing surfaces and/or products. In some aspects, the invention includes methods of using the peroxycarboxylic acid compositions to prevent biological fouling in various industrial processes and industries, including oil and gas operations, to control microorganism growth, eliminate microbial contamination, limit or prevent biological fouling in liquid systems, process waters or on the surfaces of equipment that come in contact with such liquid systems. As referred to herein, microbial contamination can occur in various industrial liquid systems including, but not limited to, air-borne contamination, water make-up, process leaks and improperly cleaned equipment. In another aspect, the peroxycarboxylic acid compositions are used to control the growth of microorganisms in water used in various oil and gas operations. In a further aspect, the compositions are suitable for incorporating into fracturing fluids to control or eliminate microorganisms.

For the various industrial processes disclosed herein, "liquid system" refers to flood waters or an environment within at least one artificial artifact, containing a substantial amount of liquid that is capable of undergoing biological fouling, it includes but is not limited to industrial liquid systems, industrial water systems, liquid process streams, industrial liquid process streams, industrial process water systems, process water applications, process waters, utility waters, water used in manufacturing, water used in industrial services, aqueous liquid streams, liquid streams containing two or more liquid phases, and any combination thereof.

In at least one embodiment this technology would be applicable to any process or utility liquid system where microorganisms are known to grow and are an issue, and biocides are added. Examples of some industrial process water systems where the method of this invention could be applied are in process water applications (flume water, shower water, washers, thermal processing waters, brewing, fermentation, CIP (clean in place), hard surface sanitization, etc.), Ethanol/Bio-fuels process waters, pretreatment and utility waters (membrane systems, ion-exchange beds), water used in the process/manufacture of paper, ceiling tiles, fiber board, microelectronics, E-coat or electro deposition applications, process cleaning, oil exploration and energy services (completion and work over fluids, drilling additive fluids, fracturing fluids, flood waters, etc.; oil fields—oil and gas wells/flow line, water systems, gas systems, etc.), and in particular water systems where the installed process equipment exhibits lowered compatibility to halogenated biocides.

The methods by which the peroxycarboxylic acid compositions are introduced into the aqueous fluids or liquid systems are not critical. Introduction of the peracid compositions may be carried out in a continuous or intermittent manner and will depend on the type of water and/or liquid being treated. In some embodiments, the peracid compositions are introduced into an aqueous fluid according to the methods disclosed in U.S. patent application Ser. No. 13/645,671, titled "New Method and Arrangement for Feeding Chemicals into a Hydrofracturing Process and Oil and Gas Applications", which is hereby incorporated by reference in its entirety.

The various applications of use described herein provide the peroxycarboxylic acid compositions to a surface, liquid and/or product in need of antimicrobial and/or sanitizing treatment. Beneficially, the compositions of the invention are fast-acting. However, the present methods require a certain minimal contact time of the compositions with the surface, liquid and/or product in need of treatment for occurrence of sufficient antimicrobial effect. The contact time can vary with concentration of the use compositions, method of applying the use compositions, temperature of the use compositions, pH of the use compositions, amount of the surface, liquid and/or product to be treated, amount of soil or substrates on/in the surface, liquid and/or product to be treated, or the like. The contact or exposure time can be at least about 15 seconds. In some embodiments, the exposure time is about 1 to 5 minutes. In other embodiments, the exposure time is at least about 10 minutes, 30 minutes, or 60 minutes. In other embodiments, the exposure time is a few minutes to hours. In other embodiments, the exposure time is a few hours to days. The contact time will further vary based upon the concentration of peracid in a use solution.

The present methods can be conducted at any suitable temperature. In some embodiments, the present methods are conducted at a temperature ranging from about 0° C. to about 70° C., e.g., from about 0° C. to about 4° C. or 5° C., from about 5° C. to about 10° C., from about 11° C. to about 20° C., from about 21° C. to about 30° C., from about 31° C. to about 40° C., including at about 37° C., from about 41° C. to about 50° C., from about 51° C. to about 60° C., or from about 61° C. to about 70° C.

The compositions are suitable for antimicrobial efficacy against a broad spectrum of microorganisms, providing broad spectrum bactericidal and fungistatic activity. For example, the peracid biocides of this invention provide broad spectrum activity against wide range of different types of microorganisms (including both aerobic and anaerobic microorganisms), including bacteria, yeasts, molds, fungi, algae, and other problematic microorganisms.

The present methods can be used to achieve any suitable reduction of the microbial population in and/or on the target or the treated target composition. In some embodiments, the present methods can be used to reduce the microbial population in and/or on the target or the treated target composition by at least one log 10. In other embodiments, the present methods can be used to reduce the microbial population in and/or on the target or the treated target composition by at least two log 10. In still other embodiments, the present methods can be used to reduce the microbial population in and/or on the target or the treated target composition by at least three log 10.

The peroxycarboxylic acid compositions may include concentrate compositions or may be diluted to form use compositions. In general, a concentrate refers to a composition that is intended to be diluted with water to provide a use solution that contacts a surface, liquid and/or product in need of treatment to provide the desired cleaning, sanitizing or the like. The peroxycarboxylic acid composition that contacts the surface, liquid and/or product in need of treatment can be referred to as a concentrate or a use composition (or use solution) dependent upon the formulation employed in methods according to the invention. It should be understood that the concentration of the peroxycarboxylic acid in the composition will vary depending on whether the composition is provided as a concentrate or as a use solution.

A use solution may be prepared from the concentrate by diluting the concentrate with water at a dilution ratio that provides a use solution having desired sanitizing and/or other antimicrobial properties. The water that is used to dilute the concentrate to form the use composition can be referred to as water of dilution or a diluent, and can vary from one location to another. The typical dilution factor is between approximately 1 and approximately 10,000 but will depend on factors including water hardness, the amount of soil to be removed and the like. In an embodiment, the concentrate is diluted at a ratio of between about 1:10 and about 1:10,000 concentrate to water. Particularly, the concentrate is diluted at a ratio of between about 1:100 and about 1:5,000 concentrate to water. More particularly, the concentrate is diluted at a ratio of between about 1:250 and about 1:2,000 concentrate to water.

The contents of all references, patents, and patent applications cited throughout this application are hereby incorporated by reference to the same extent as if each individual publication or patent application was specifically and individually indicated as incorporated by reference. All publications and patent applications in this specification are indicative of the level of ordinary skill in the art to which this invention pertains. The invention is further illustrated by the following examples, which should not be construed as further limiting.

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications to the embodiments of the invention to adapt it to various usages and conditions.

EXAMPLES

Example 1

Synthesis of Solid Supported Peracid Stabilizer

The synthesis of dipicolinic acid (DPA) functionalized polystyrene resins as depicted in FIG. 3 was completed. Poly(styrene-co-vinylbenzylchloride-co-divinylbenzene) resin beads were used as solid support and chelidamic acid was used as the DPA moiety. The chelidamic acid was attached through covalent bonding to the polymer backbone via an ether linkage. The synthesis of solid-supported stabilizers was achieved in the following three steps:

1. Chelidamic acid has built-in DPA-like structures and is used to couple to a polystyrene backbone via acid catalyzed esterification of dimethyl ester of Chelidamic acid with methanol. The reaction took place with 10 mL chelidamic acid, 50 mL methanol and 0-2 mL sulfuric acid. The chelidamic acid was dissolved in methanol and two drops of sulfuric acid were added. The reaction was refluxed at 65° C. for 5 hours. The solvent was removed and solids were washed with water. The solid was air dried for 10 hours.

2. DPA moiety was installed on the poly(styrene-co-vinylbenzylchloride-co-divinylbenzene) resin backbone via base catalyzed reaction alkylation reaction between chlormethyl groups on resin and dimethyl ester of Chelidamic acid. Chlormethylated polystyrene was the starting material. Chloromethylated polystyrene beads (Cl loading=5.1 meq/g, 20 g) were left for swelling in dimethylformamide (100 mL) for 2 hours. Dimethyl ester of Chelidamic acid (20.1 g) and potassium carbonate (12.2 g) were added. Resulting suspension was under heated and stirring at 80° C. for 24 hours. After cooling, the reaction mixture was filtered using fritted glass funnel under vacuum, washed sequentially with acetone, dichloromethane, tetrahydrofuran, water, acetone and dried at 70° C. overnight.

3. DPA-functionalized resin was subjected to hydrolysis to generate carboxylic acid groups of DPA moieties. Resin beads (14.2 g) were left for swelling in dichlorethane. A 50% KOH solution (12.5 g KOH and 12.5 g water) (25 g) was added to the resin beads. 2 g Adogen 464 (1.99 g) were added and then the resin beads were placed in a nitrogen blanket under heated and stirring at 70° C. for 48 hours. Resulting suspension was under heated and stirring at 80° C. for 24 hours. After cooling, the reaction mixture was filtered using fritted glass funnel under vacuum, washed sequentially with acetone, dichloromethane, tetrahydrofuran, water, acetone and dried at 80° C. overnight.

The resulting resin was analyzed by FT-IR to confirm the polymer structure and then used for performance testing according to the following Examples.

Example 2

Stability Comparison of Peracetic Acid Compositions with DPA-Polymer Stabilizer

The resin containing the DPA polymer synthesized in Example 1 (8275-3) was used to assess stabilization of a peroxyacetic acid composition. Compositions of peracetic acid with and without the DPA polymer were evaluated as shown in Table 2. The negative control (Composition 1) does not include the dipicolinic acid polymer, whereas the positive control (Composition 0) HEDP). The positive controls compare formulations using the conventional peracid stabilizer HEDP to those including DPA, both in a non-polymeric form in solution with the peroxyacetic acid. The positive control formulations also used the catalyst sulfuric acid as opposed to phosphoric acid, however this difference does not result in any significant difference in peroxyacetic acid concentration and/or the stability of the formulation, as the mineral acid is used as a catalyst for the formation of the peroxyacetic acid. In Tables 3-4 there were differences in measured PAA % at Time 0 because each version after formulation (pre-equilibration) produced different maxima PAA % (post formulation). As one skilled in the art will ascertain, even if each PAA formulation started with the same potential PAA their respective intrinsic stabilities affect PAA % maximum achieved.

TABLE 3

| Time (days at 40° C.) | Sample | | | | | |
|---|---|---|---|---|---|---|
| | Composition 1 (Neg. Control) | | Composition 2 | | Composition 3 | |
| | PAA % | $H_2O_2$ % | PAA % | $H_2O_2$ % | PAA % | $H_2O_2$ % |
| 0 | 12.70 | 10.38 | 14.25 | 11.15 | 13.40 | 11.27 |
| 20 | 9.52 | 7.99 | 14.09 | 11.05 | 13.02 | 10.54 |
| 45 | 5.44 | 4.36 | 13.75 | 9.99 | 11.55 | 8.41 |
| % Lost | 42.83 | 42.00 | 3.51 | 8.99 | 10.55 | 10.53 |
| % Retained | 57.17 | 58.00 | 96.49 | 91.01 | 89.45 | 89.47 |

As shown in Table 3, the stability of both peracetic acid and $H_2O_2$ are significantly improved in the presence of as low as 0.5% DPA polymer, where the Compositions 2 and 3 each achieve stability at 45 days of 91% and 89.5%, respectively, % PAA retained. Further increase of the amount of DPA polymer in the composition see diminishing stability improvement, although still provides significant improvement of the Composition 1 formulation where a 42% per

TABLE 2

| Raw Material | Composition 0 (Positive Control-DPA) (wt-%) | Composition 0 (Positive Control-HEDP) (wt-%) | Composition 1 (Negative Control) (wt-%) | Composition 2 (wt-%) | Composition 3 (wt-%) |
|---|---|---|---|---|---|
| Acetic acid | 43.85 | 43.85 | 43.85 | 43.85 | 43.85 |
| $H_2O_2$(35%) | 50.85 | 50.85 | 50.85 | 50.85 | 50.85 |
| $H_3PO_4$ (75%) | 0.00 | 0.00 | 0.90 | 0.90 | 0.90 |
| $H_2SO_4$ (50%) | 1.00 | 1.00 | 0.00 | 0.00 | 0.00 |
| HEDP (60%) | 0.00 | 1.50 | 0.00 | 0.00 | 0.00 |
| Dipicolinic acid polymer | 0.50 | 0.00 | 0.00 | 0.50 | 1.00 |
| DI water | 4.25 | 3.25 | 4.40 | 4.35 | 3.4 |
| Total | 100 | 100 | 100 | 100. | 100 |

The stability of the generated peracetic acid as well as $H_2O_2$ were monitored by iodometric titration, and the results are summarized in Table 3 for Compositions 1-3 and Table 4 for the positive controls (Composition 0—DPA and acetic acid lost and 42% hydrogen peroxide loss was observed. The Composition 1 fails to provide the claimed benefit of retaining at least 80% PAA content after 30 days storage at a temperature of at least 40° C.

TABLE 4

| Sample Time | Composition 0 (Pos. Control - DPA) | | Composition 0 (Pos. Control - HEDP) | |
| --- | --- | --- | --- | --- |
| (days at 40° C.) | PAA % | H$_2$O$_2$ % | PAA % | H$_2$O$_2$ % |
| 0 | 15.00 | 10.00 | 15.00 | 10.00 |
| 14 | 14.73 | 11.50 | 14.31 | 10.96 |
| 49 | 14.18 | 10.60 | 10.48 | 8.27 |
| % Lost | 5.47% | N/A | 30.13% | 17.3% |
| % Retained | 94.53% | 106.00% | 69.87% | 82.7% |

The stability of the positive control formulations shows that the resin containing the DPA polymer synthesized in Example 1 provides at least the same or improved stability to the peroxyacetic acid composition than the positive control (non-polymeric DPA) at the evaluated time intervals, where the peracid stabilizer as described herein provided about 96.5% retained PAA concentration at 45 days compared to 94.5% retained PAA concentration at 49 days for the positive control.

All publications and patent applications in this specification are indicative of the level of ordinary skill in the art to which this invention pertains. All publications and patent applications are herein incorporated by reference to the same extent as if each individual publication or patent application was specifically and individually indicated by reference. The disclosure of each reference set forth herein is incorporated herein by reference in its entirety. The invention has been described with reference to various specific and preferred embodiments and techniques. However, it should be understood that many variations and modifications may be made while remaining within the spirit and scope of the invention.

What is claimed is:

1. A method of stabilizing a peroxycarboxylic acid composition comprising:
    esterifying an acid comprising chelidamic acid to generate a dimethyl ester of chelidamic acid;
    contacting the dimethyl ester of chelidamic acid with a resin material comprising poly(styrene-co-vinylbenzyl-chloride-co-divinylbenzene) in an alkylation reaction between one or more chlormethyl groups on the resin and the dimethyl ester of chelidamic acid to generate a functionalized resin;
    hydrolyzing the functionalized resin to generate a dipicolinic acid-functionalized resin comprising one or more carboxylic acid groups; and
    providing the dipicolinic acid-functionalized resin to a peroxycarboxylic acid composition in need of stabilization;
    wherein the peroxycarboxylic acid composition comprises a C$_1$-C$_{22}$ carboxylic acid, a C$_1$-C$_{22}$ percarboxylic acid, hydrogen peroxide, and water, and
    wherein the peroxycarboxylic acid composition retains at least about 80% of the peroxycarboxylic acid after 30 days storage at a temperature of at least 40° C. and up to 70° ° C.

2. The method of claim 1, wherein the resin material is crosslinked.

3. The method of claim 1, wherein the peroxycarboxylic acid composition comprises from about 1 wt-% to about 80 wt-% of the C$_1$-C$_{22}$ carboxylic acid.

4. The method of claim 1, wherein the peroxycarboxylic acid composition comprises from about 1 wt-% to about 80 wt-% of the hydrogen peroxide.

5. The method of claim 1, wherein the peroxycarboxylic acid composition comprises from about 0.1 wt-% to about 1 wt-% of the dipicolinic acid-functionalized resin.

6. The method of claim 1, wherein the peroxycarboxylic acid composition retains at least about 85% of peroxycarboxylic acid after 30 days storage at a temperature of at least 40° C. and up to 70° C.

7. The method of claim 1, wherein the dipicolinic acid-functionalized resin is added into a container of the peroxycarboxylic acid composition or applied as a coating to a surface of a container in contact with the peroxycarboxylic acid composition, and wherein the container houses the peroxycarboxylic acid composition during storage and/or transport.

8. A stabilized peroxycarboxylic acid composition comprising the dipicolinic acid-functionalized resin and peroxycarboxylic acid composition prepared in claim 1.

9. The composition of claim 8, wherein the composition comprises from about 1 wt-% to about 80 wt-% of the C$_1$-C$_{22}$ carboxylic acid.

10. The composition of claim 8, wherein the composition comprises from about 1 wt-% to about 80 wt-% of the hydrogen peroxide.

11. The composition of claim 8, wherein the composition comprises from about 0.1 wt-% to about 1 wt-% of the dipicolinic acid-functionalized resin.

12. The composition of claim 8, further comprising at least one additional agent comprising a surfactant, a hydrotrope, a defoaming agent, a solvent, a mineral acid, or a combination thereof.

* * * * *

UNITED STATES PATENT AND TRADEMARK OFFICE
CERTIFICATE OF CORRECTION

| | |
|---|---|
| PATENT NO. | : 12,096,768 B2 |
| APPLICATION NO. | : 16/947585 |
| DATED | : September 24, 2024 |
| INVENTOR(S) | : Ashish Dhawan et al. |

Page 1 of 1

It is certified that error appears in the above-identified patent and that said Letters Patent is hereby corrected as shown below:

In the Claims

<u>In Claim 1, Column 31, Approx. Line 43:</u>
DELETE: "chlormethyl"
INSERT: --chloromethyl--

Signed and Sealed this
First Day of April, 2025

Coke Morgan Stewart
*Acting Director of the United States Patent and Trademark Office*